United States Patent [19]

Wenger et al.

[11] Patent Number: 4,941,909
[45] Date of Patent: Jul. 17, 1990

[54] HETEROCYCLIC COMPOUNDS

[75] Inventors: Jean Wenger, Uster; Paul Winternitz, Greifensee; Martin Zeller, Dübendorf, all of Switzerland

[73] Assignee: Hoffmann-La Roche Inc., Nutley, N.J.

[21] Appl. No.: 334,952

[22] PCT Filed: Jun. 16, 1988

[86] PCT No.: PCT/CH88/00107
§ 371 Date: Feb. 14, 1989
§ 102(e) Date: Feb. 14, 1989

[87] PCT Pub. No.: WO88/10254
PCT Pub. Date: Dec. 29, 1988

[30] Foreign Application Priority Data

Jun. 19, 1987 [CH] Switzerland .................. 2320/87
Sep. 17, 1987 [CH] Switzerland .................. 3580/87

[51] Int. Cl.$^5$ .................. A01N 43/54; A01N 43/10; C07D 239/54
[52] U.S. Cl. .................. 71/92; 71/90; 544/209; 544/310; 544/311; 544/312; 544/313; 544/314
[58] Field of Search ............ 544/309, 310, 311, 312, 544/313, 314; 71/90, 92

[56] References Cited

U.S. PATENT DOCUMENTS 4,746,352 5/1988 Wenger et al. .................. 544/311

OTHER PUBLICATIONS

Wenger et al, CA 106-50241g (1987), "Aryluracils and Their Use as Herbicides".
Wenger et al, CA 109-231048g (1988), "Preparation of Herbicidal 3-Aryluracil Enol Ethers".
Wenger et al., CA 110-231655y (1989), "Preparation of Pyrimidinylbenzoates as Herbicides".

Primary Examiner—Cecilia Shen
Attorney, Agent, or Firm—George M. Gould; William H. Epstein; Dennis P. Tramaloni

[57] ABSTRACT

The invention is concerned with novel compounds of the formula

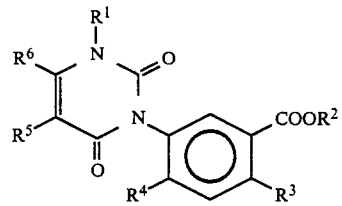

wherein $R^1$, $R^2$, $R^3$, $R^4$, $R^5$ and $R^6$ have the significances given in the description, as well as enol ethers and salts thereof and their manufacture, weed control compositions which contain such compounds as active substances and the use of the active substances or compositions for the control of weeds. The invention is also concerned with certain starting materials which have herbicidal activity and with weed control compositions containing these.

19 Claims, No Drawings

HETEROCYCLIC COMPOUNDS

The present invention is concerned with heterocyclic compounds, namely 3-aryluracils of the general formula I

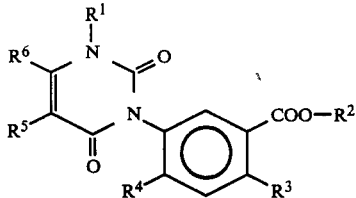

wherein
$R^1$ signifies hydrogen, $C_{1-4}$-alkyl, $C_{3\ or\ 4}$-alkenyl, $C_{3\ or\ 4}$-alkynyl or $C_{1-4}$-haloalkyl,
$R^2$ signifies a group

or, where $R^1$ signifies haloalkyl, also hydrogen, $C_{1-8}$-alkyl, $C_{2-8}$-alkenyl, $C_{2-8}$-alkynyl or $C_{2-8}$-alkoxyalkyl,
$R^3$ signifies halogen or cyano,
$R^4$ signifies hydrogen or halogen,
$R^5$ signifies hydrogen, fluorine or $C_{1-4}$-alkyl,
$R^6$ signifies $C_{1-4}$-alkyl or $C_{1-4}$-haloalkyl, the symbols $R^7$ each independently signify hydrogen or $C_{1-3}$-alkyl and
n signifies 0, 1 or 2, and
Q signifies a saturated three- to seven-membered carbocyclic or heterocyclic residue which is optionally substituted with one or more $C_{1-4}$-alkyl residues, whereby the heterocyclic residue has 1 or 2 hetero atoms selected from oxygen and sulphur and optionally a keto function in the ring, or
Q signifies a phenyl residue which is optionally mono- or multiply-substituted with halogen, $C_{1-4}$-alkyl, $C_{1-4}$-haloalkyl, $C_{1-4}$-alkoxy, $C_{1-4}$-alkylthio, nitro and/or cyano and which additionally can contain a fused, saturated, carbocyclic or heterocyclic five- to seven-membered ring, whereby the heterocycle has 1 or 2 oxygen atoms in the ring,
and the corresponding enol ethers of those compounds of formula I in which $R^1$ is different from hydrogen or $C_{1-4}$-haloalkyl as well as salts of those compounds of formula I in which $R^1$ or $R^2$ signifies hydrogen.

Under the aforementioned enol ethers there are thus to be understood the compounds of the formula

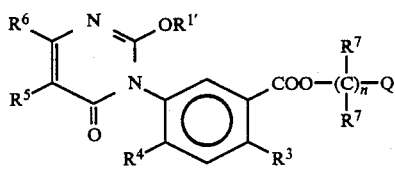

wherein $R^3$, $R^4$, $R^5$, $R^6$, $R^7$, n and Q have the significances given above and $R^{1'}$ signifies $C_{1-4}$-alkyl, $C_{3\ or}$ 4-alkenyl or $C_{3\ or}$ 4-alkynyl.

The compounds in accordance with the invention have herbicidal activity and are suitable as active substances of weed control compositions. Accordingly, the invention also includes weed control compositions which contain compounds in accordance with the invention as the active substance, a process for the manufacture of these compounds as well as the use of the compounds or compositions for the control of weeds.

In formula I above "halogen" embraces fluorine, chlorine, bromine and iodine. The alkyl, alkenyl and alkynyl residues can be straight-chain or branched and this also applies to the alkyl part of the haloalkyl, alkoxy and alkylthio groups. A haloalkyl group can have one or more (similar or different) halogen atoms.

The following are examples of residues Q: Cyclopropyl, cyclobutyl, cyclopentyl, cyclohexyl, cycloheptyl, 2-oxiranyl, 2-methyl-2-oxiranyl, 3-oxetanyl, 3-methyl-3-oxetanyl, 3-ethyl-3-oxetanyl, 2-tetrahydrofuryl, 3-tetrahydrofuryl, 2-tetrahydropyranyl, 3-tetrahydropyranyl, 4-tetrahydropyranyl, 3-methyl-3-thietanyl, 3-tetrahydrothienyl, 1,3-dioxolan-5-yl, 1,3-dioxan-5-yl, 1-oxo-4-tetrahydrothiopyranyl, phenyl, 1,3-benzodioxol-5-yl and 1,3-benzodioxan-6-yl.

The salts of the compounds of formula I are especially alkali metal salts, e.g. sodium and potassium salts; alkaline earth metal salts, e.g. calcium and magnesium salts; ammonium salts, i.e. unsubstituted ammonium salts and mono- or multiply-substituted ammonium salts, e.g. triethylammonium and methylammonium salts, as well as salts with other organic bases, e.g. with pyridine.

The presence of at least one asymmetric carbon atom in the compounds of formula I means that the compounds can occur in optically isomeric forms. Geometric isomerism can also occur when an aliphatic C=C double bond is present. Formula I is intended to embrace all of these possible isomeric forms as well as mixtures thereof.

An interesting group of compounds in accordance with the invention comprises those compounds of formula I in which $R^1$ signifies hydrogen $C_{1-4}$-alkyl, $C_{3\ or}$ 4-alkenyl or $C_{3\ or}$ 4-alkynyl and the enol ethers and salts of these compounds. A further interesting group of compounds in accordance with the invention comprises those compounds of formula I in which $R^1$ signifies $C_{1-4}$-haloalkyl, $R^2$ signifies hydrogen, $C_{1-8}$-alkyl, $C_{2-8}$-alkenyl, $C_{2-8}$-alkynyl, $C_{2-8}$-alkoxyalkyl or a group $-(CR^7R^7)_n-Q$ and Q signifies either a saturated three- to seven-membered carbocyclic or heterocyclic residue which is optionally substituted with one or more $C_{1-4}$-alkyl residues, whereby the heterocyclic residue has 1 or 2 hetero atoms selected from oxygen or sulphur in the ring, or a phenyl residue which is optionally mono- or multiply-substituted with halogen, $C_{1-4}$-alkyl, $C_{1-4}$-haloalkyl, $C_{1-4}$-alkoxy, $C_{1-4}$-alkylthio, nitro and/or cyano, and the salts of these compounds.

If $R^1$ signifies $C_{3\ or\ 4}$-alkenyl or $C_{3\ or\ 4}$-alkynyl, this residue is preferably allyl or propargyl. Where $R^6$ signifies haloalkyl, this is preferably trifluoromethyl or pentafluoroethyl. In general a halogen atom which may be present is preferably fluorine, chorine or bromine.

Independently of one another $R^1$ preferably signifies straight-chain $C_{1-4}$-alkyl, especially methyl, or $C_{1-4}$-fluoroalkyl, especially difluoromethyl; $R^3$ preferably signifies chlorine or bromine; $R^4$ preferably signifies hydrogen or fluorine; $R^5$ preferably signifies hydrogen, fluorine or methyl; $R^6$ preferably signifies $C_{1-4}$-alkyl, especially methyl; each $R^7$ preferably signifies hydrogen; and n preferably signifies 0 or 1.

Especially preferred compounds of formula I are the cycloheptyl, 3-tetrahydrofuryl, 1,3-dioxan-5-yl, cyclopropylmethyl, tetrahydrofurfuryl, 1,3-dioxolan-4-ylmethyl, benzyl, 4,4-dimethyl-2-oxo-tetrahydrofuran-3-yl, cyclopentyl, 1-cyclopropylethyl and cyclohexyl esters of 2-chloro-5-[3,6-dihydro-2,6-dioxo-3-methyl-4-trifluoromethyl-1(2H)-pyrimidinyl]-4-fluorobenzoic acid.

Further representatives of compounds of formula I are the 3-nitrobenzyl, α,α-dimethylbenzyl, tetrahydrothiophen-3-yl, 4-cyanophenyl and 3,5-di(trifluoromethyl)benzyl esters of 2-chloro-5-[3,6-dihydro-2,6-dioxo-3-methyl-4-trifluoromethyl-1(2H)-pyrimidinyl]-4-fluorobenzoic acid as well as the cyclopropylmethyl, 1-cyclopropylethyl, cyclopentyl, cyclohexyl, cycloheptyl, 3-tetrahydrofuryl, 1,3-dioxan-5-yl, 1,3-dioxolan-4-ylmethyl, benzyl and tetrahydrofurfuryl esters of 2-chloro-5-[3,6-dihydro-3,4-dimethyl-2,6-dioxo-1(2H)-pyrimidinyl]-4-fluorobenzoic acid.

Especially preferred compounds of formula I in which $R^1$ signifies $C_{1-4}$-haloalkyl are:

Isopropyl 2-chloro-5-[3-difluoromethyl-3,6-dihydro-4-methyl-2,6-dioxo-1(2H)-pyrimidinyl]-4-fluorobenzoate, 2-chloro-5-[3-difluoromethyl-3,6-dihydro 4-methyl-2,6-dioxo-1(2H)-pyrimidinyl]-4-fluorobenzoic acid, isopropyl 5-[4-ethyl-3-difluoromethyl-3,6-dihydro-2,6-dioxo-1(2H)-pyrimidinyl]-2-chloro-4-fluorobenzoate, isopropyl 5-[4-ethyl-3-difluoromethyl-3,6-dihydro-2,6-dioxo-1(2H)-pyrimidinyl]-2-bromo-4-fluorobenzoate, isopropyl 2-bromo-5-[3-difluoromethyl-3,6-dihydro-4-methyl-2,6-dioxo-1(2H)-pyrimidinyl]-4-fluorobenzoate, 2-propynyl-2-chloro-5-[3-difluoromethyl-3,6-dihydro-4-methyl-2,6-dioxo-1(2H)-pyrimidinyl]-4-fluorobenzoate and methyl 2-chloro-5-[3-difluoromethyl-3 6-dihydro-4-methyl-2,6-dioxo-1(2H)-pyrimidinyl]-4-fluorobenzoate.

Further representatives of such compounds of formula I are the ethyl, n-propyl, n-butyl, n-hexyl n-octyl, sec.-butyl, 1-methylbutyl, neopentyl, isobutyl, isopentyl, 2-methylbutyl, 1,2-dimethylpropyl, tert.butyl, 1-ethylpropyl, allyl, 2-butenyl, 3-methyl-2-butenyl, 3-methyl-3-butenyl 1-ethyl-2-propenyl, 4-pentenyl, 1-methyl-2-butenyl, 1-methyl-3-butenyl, 3-butenyl, 2-methyl-2-propenyl, 3-butynyl, 2-butynyl, methoxymethyl, ethoxymethyl, n-propoxymethyl, isopropoxymethyl, n-pentyloxymethyl, 1-methoxyethyl, 2-methoxyethyl 2-ethoxyethyl, 2-isopropoxyethyl, 2-methoxy-1-methylethyl, 2-n-butyloxyethyl, cyclopentyl, cyclohexyl, cycloheptyl, cyclopropylmethyl, 1-cyclopropylethyl, 3-tetrahydrofuryl, tetrahydrofurfuryl, 1,3-dioxan-5-yl, 1,3-dioxolan-5-ylmethyl, benzyl and 4-methoxyphenyl esters of 2-chloro-5-[3-difluoromethyl-3,6-dihydro-4-methyl-2,6-dioxo-1(2H)-pyrimidinyl]-4-fluorobenzoic acid, isopropyl 2-chloro-5-[3-difluoromethyl-3,6-dihydro-4,5-dimethyl-2,6-dioxo-1(2H)-pyrimidinyl]-4-fluorobenzoate, isopropyl 2-chloro-5-[3-difluoromethyl-3,6-dihydro-5-fluoro-4-methyl-2,6-dioxo-1(2H)-pyrimidinyl]-4-fluorobenzoate, isopropyl 2-chloro-5-[3-difluoromethyl-3,6-dihydro-4-methyl-2 6-dioxo-1(2H)-pyrimidinyl]-benzoate and isopropyl 2-chloro-5-[3,6-dihydro-4-methyl-3-(1,1,2,2-tetrafluoroethyl)-2,6-dioxo-1(2H)-pyrimidinyl]-4-fluorobenzoate.

The process in accordance with the invention for the manufacture of the compounds of formula I and of their enol ethers as well as salts is characterized by (a) for the manufacture of those compounds of formula I in which $R^1$ signifies hydrogen as well as, if desired, of metal salts of these compounds, subjecting a compound of the general formula

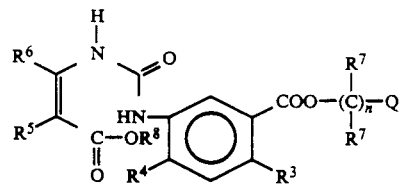

wherein $R^3$, $R^1$, $R^5$, $R^6$, $R^7$, n and Q have the significances given above and $R^8$ signifies lower alkyl, preferably $C_{1-4}$-alkyl, to a cyclization under basic conditions and, if desired, converting a metal salt of the uracil derivative of formula I which may be obtained into the acid form ($R^1$=hydrogen) by treatment with an acid, (b) for the manufacture of those compounds of formula I in which $R^1$ signifies $C_{1-4}$-alkyl, $C_{3\ or\ 4}$-alkenyl, $C_{3\ or\ 4}$-alkynyl or $C_{1-4}$-haloalkyl, whereby $R^2$ is different from hydrogen when $R^1$ signifies $C_{1-4}$-haloalkyl, subjecting a uracil derivative of the general formula

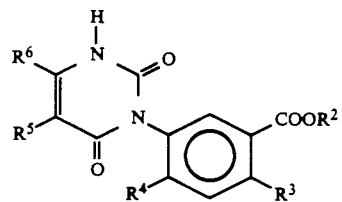

wherein $R^2$, $R^3$, $R^4$, $R^5$ and $R^6$ have the significances given above, to an alkylation with a corresponding alkylating agent containing a $C_{1-4}$-alkyl, $C_{3\ or\ 4}$-alkenyl or $C_{3\ or\ 4}$-alkynyl group, with the proviso that in the manufacture of a compound of formula I in which $R^1$ signifies $C_{1-4}$-haloalkyl $R^2$ in formula I' is different from hydrogen, (c) for the manufacture of those compounds of formula I in which $R^1$ is different from hydrogen and of the corresponding enol ethers, esterifying a benzoic acid of the general formula

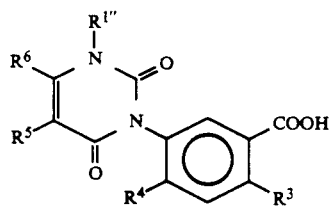

wherein $R^3$, $R^4$, $R^5$ and $R^6$ have the significances given above and $R^{1'''}$ signifies $C_{1-4}$-alkyl, $C_{3\ or\ 4}$-alkenyl, $C_{3\ or\ 4}$-alkynyl or $C_{1-4}$-haloalkyl, or the corresponding enol ether, whereby the benzoic acid or its enol ether can be present in the form of a reactive derivative, with a hydroxy compound of the general formula

R²OH        IV wherein R² has the significance given above with the proviso that in the manufacture of a compound of formula I in which R¹ signifies $C_{1-4}$-haloalkyl R² in formula IV is different from hydrogen, or with a reactive derivative of this hydroxy compound, (d) for the manufacture of those compounds of formula I in which R¹ is different from hydrogen, subjecting a benzoic acid ester of the general formula

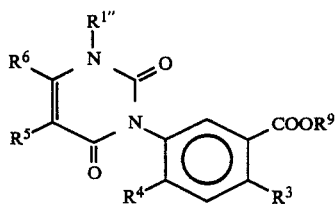

V wherein $R^{1''}$, $R^3$, $R^4$, $R^5$ and $R^6$ have the significances given above and $R^9$ signifies $C_{1-6}$-alkyl, $C_{2-4}$-alkenyl, $C_{2-4}$-alkynyl or $C_{2-6}$-alkoxyalkyl, to a trans-esterification reaction with a hydroxy compound of formula IV given above, whereby the reagent IV has a higher boiling point than the alkanol, alkenol or alkynol R⁸OH, or (e) for the manufacture of those compounds of formula I in which R¹ signifies $C_{1-4}$-haloalkyl and R signifies hydrogen, hydrolyzing a benzoic acid ester of the general formula

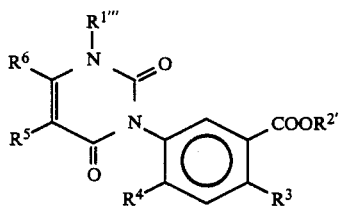

I'' wherein $R^3$, $R^4$, $R^5$ and $R^6$ have the significances given above and $R'''$ signifies $C_{1-4}$-haloalkyl and $R^{2'}$ has the significance of $R^2$ with the exception of hydrogen, to the corresponding benzoic acid, (f) for the manufacture of the enol ethers of the compounds of formula I, treating a uracil derivative of the general formula

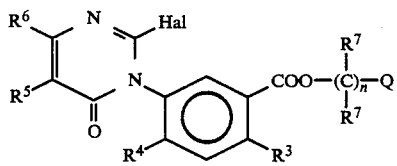

VI wherein $R^3$, $R^4$, $R^5$, $R^6$, $R^7$, n and Q have the significances given above and Hal signifies chlorine or bromine, with an alkanol, alkenol or alkynol $R^{1'}$OH in the presence of an organic base or with the corresponding alcoholate, alkenolate or alkynolate of the general formula

 VII wherein $R^{1'}$ has the significance given above and $M^\oplus$ signifies an equivalent of a metal ion.

and, if desired, converting a thus-obtained compound of formula I in which R¹ or R² signifies hydrogen into a salt.

The cyclization according to process variant (a) can be carried out conveniently by treating the compound of formula II in an inert protic organic solvent such as an alcohol, e.g. methanol, ethanol or isopropanol; an inert aprotic organic solvent such as an aliphatic or cyclic ether, e.g. 1,2-dimethoxyethane, tetrahydrofuran or dioxan or an aromatic, e.g. benzene or toluene; an inert aprotic, polar organic solvent, e.g. dimethylformamide or dimethyl sulphoxide, whereby such solvents can be optionally used in a two-phase mixture with a hydrocarbon, e.g. n-hexane or toluene; or water with a base at temperatures between −78° C. and the reflux temperature of the reaction mixture. As bases there preferably come into consideration sodium alcoholates, alkali metal hydroxides, especially sodium hydroxide and potassium hydroxide, alkali metal carbonates, especially sodium carbonate and potassium carbonate, and sodium hydride. Where an alkanol is used as the solvent, this solvent conveniently corresponds to the respective hydroxy compound $Q$-$(CR^7R^7)_n$-OH; thereby undesired concurrent trans-esterification reactions are avoided. When sodium hydride is used as the base, the solvent is preferably an aliphatic or cyclic ether, dimethylformamide or dimethyl sulphoxide, whereby any of these solvents can be used in admixture with toluene.

Where one of the above-mentioned bases or the like is used, after completion of the cyclization the product is present in the form of the corresponding alkali metal salt. This can be isolated and purified in a manner known per se or the mixture can be acidified in order to isolate the respective compound of formula I itself. For this purpose there is preferably used a mineral acid such as hydrochloric acid or a strong organic acid such as acetic acid or p-toluenesulphonic acid.

In process variant b) the term "alkylation" stands for the substitution of the hydrogen atom of the $N^1$-atom of the uracil nucleus with a $C_{1-4}$-alkyl, $C_{3\ or\ 4}$-alkenyl, $C_{3\ or\ 4}$-alkynyl or $C_{1-4}$-haloalkyl group. As the alkylating agent there is conveniently used a $C_{1-4}$-alkyl, $C_{3\ or\ 4}$-alkenyl or $C_{3\ or\ 4}$-alkynyl halide, especially the respective chloride or bromide, or sulphate, or a multiply-halogenated $C_{1-4}$-alkane such as, for example, chlorodifluoromethane or a mono- or multiply-halogenated alkene such as, for example, tetrafluoroethene.

The alkylation is conveniently carried out in the presence of an inert, protic organic solvent such as lower alkanol, e.g. ethanol, optionally in admixture with water; an inert, aprotic organic solvent such as an aliphatic or cyclic ether, e.g. 1,2-dimethoxyethane, tetrahydrofuran or dioxan; a ketone, e.g. acetone or butan-2-one; or an inert, aprotic, polar organic solvent, e.g. dimethylformamide, dimethyl sulphoxide or acetonitrile, as well as in the presence of a base such as sodium hydride, an alkali metal hydroxide, especially sodium or potassium hydroxide, an alkali metal alcoholate, especially sodium alcoholate, or an alkali metal carbonate or bicarbonate, especially sodium carbonate, potassium carbonate, sodium bicarbonate or potassium bicarbonate, at temperatures between 0° C. and the reflux temperature of the reaction mixture preferably at room temperature, or, in the case of the substitution of the hydrogen atom of the $N^1$ atom with a $C_{1-4}$-haloalkyl group, preferably at temperatures between 50° C. and 100° C. In a preferred embodiment the uracil derivative of formula I' is firstly treated with the base such as sodium hydride, ethanolate or carbonate in the solvent and after a short reaction period is treated with the halide in the same solvent. In a further embodiment the uracil derivative I' is brought to reaction together with a dialkyl sulphate in the presence of an alkali metal bicarbonate, especially sodium or potassium bicarbonate, in the solvent, e.g. acetone, at the reflux temperature. The reaction has generally finished, depending on the solvent which is used, within a relatively short time or after several hours.

Process variant (c) is an esterification of the benzoic acid or of the enol ether or of a reactive derivative thereof, which can be carried out according to methods known per se. Thus, for example, a salt of a benzoic acid of formula III or of the corresponding enol ether is reacted with a halide, especially chloride, bromide or iodide, or the sulphate, mesylate or tosylate of the hydroxy compound IV in an inert diluent at temperatures between room temperature and 100° C., e.g. at the reflux temperature of the reaction mixture, preferably in the temperature range of 40° C. to 70° C. As salts of the benzoic acid of formula III or of the corresponding enol ether there come into consideration especially alkali metal salts, e.g. the sodium, potassium or lithium salt, alkaline earth metal salts, e.g. the magnesium, calcium or barium salt and salts with orhanic bases such as tertiary amines, e.g. triethylamine, 1,5-diaza-bicyclo[4,3,0]non-5-ene, 1,8-diaza-bicyclo[5,4,0]undec-7-ene and 1,4-diaza-bicyclo[2,2,2]octane, with the alkali metal salts, especially the sodium salt and the potassium salt, being preferred. The diluents which can be used are preferably. inert organic solvents such as lower alkanols, e.g. ethanol, aliphatic and cyclic ethers e.g. diethyl ether, 1,2-dimethoxyethane, tetrahydrofuran and dioxan ketones, e.g. acetone and 2-butanone, dimethylformamide, dimethyl sulphoxide, acetonitrile and hexamethylphosphoric acid triamide. The salt can be produced in situ by reacting the acid with a suitable inorganic base, e.g. an alkali metal or alkaline earth metal carbonate or bicarbonate, hydroxide or hydride, or organic base to give the salt and subsequently allowing this to react in the same reaction medium with the second reaction partner.

When an acid halide of the benzoic acid of formula III or of the corresponding enol ether is used as the reactive derivative, this is conveniently reacted with the hydroxy compound of formula IV in an inert organic solvent such as an aliphatic or cyclic ether, e.g. diethyl ether, 1,2-dimethoxyethane, tetrahydrofuran or dioxan, an aliphatic or aromatic hydrocarbon e.g. n-hexane, benzene or toluene, or a halogenated, especially chlorinated, hydrocarbon, e.g. methylene chloride, chloroform or carbon tetrachloride, at temperatures from about −20° C. to 100° C. preferably from 0° C. to 50° C. Moreover, the reaction is conveniently carried out in the presence of an acid-binding agent such as an organic base, e.g. triethylamine, pyridine, 1,5-diaza-bicyclo[4,3,0]non-5-ene, 1,8-diaza-bicyclo[5,4,0]undec-7-ene or 1,4-diaza-bicyclo[2,2,2]octane. The acid halide is preferably the acid chloride.

As further reactive derivatives of the benzoic acid of formula III or of the corresponding enol ether there are to be mentioned the corresponding O-acyl-1,3-dicyclohexylisourea and the corresponding N-acylimidazole or acid anhydride. Such derivatives can be reacted, like the acid halide, with the hydroxy compounds of formula IV in order to proceed to the desired benzoic acid esters. In these cases, however, the use of an acid-binding agent is unnecessary.

The reaction according to process variant (d) can be carried out conveniently by heating the benzoic acid ester of formula V in excess hydroxy compound of formula IV in the presence of a basic catalyst such as sodium cyanide, preferably at the reflux temperature of the reaction mixture. In the course of the reaction the residue $R^9$ of the benzoic acid ester V is replaced by the group $R^2$ of the hydroxy compound IV, whereby the alkanol, alkenol or alkynol $R^2OH$, which has a lower boiling point, is liberated.

The hydrolysis of the benzoic acid ester I" according to process variant (e) can be carried out according to methods known per se, especially using a strong mineral acid such as sulphuric acid or a base such an alkali metal or alkaline earth metal hydroxide, e.g. sodium hydroxide or potassium hydroxide, and optionally in the presence of an organic solvent such as an alcohol, e.g. methanol or ethanol, or a chlorinated hydrocarbon, e.g. methylene chloride, if desired also in admixture with water. The hydrolysis is conveniently effected at temperatures between −20° C. and 100° C. preferably at room temperature. Where the product is present as a salt after alkaline hydrolysis, this can be isolated, for example, by simply evaporating the solvent. The free acid can then be obtained by acidifying the salt with an acid preferably a mineral acid, e.g. hydrochloric acid or sulphuric acid.

In process variant (f) the term "metal ion" stands especially for an alkali metal ion, e.g. the sodium or potassium ion, or an alkaline earth metal ion, e.g. the calcium or magnesium ion. The sodium ion is the preferred metal ion. Where the alkanol alkenol or alkynol $R^{1'}OH$ is used, pyridine is the especially suitable organic base.

The reaction is conveniently effected in an excess of the corresponding alcohol $R^1OH$ as the diluent and at temperatures between 0° C. and 50° C., preferably at room temperature.

Insofar as they can not be manufactured directly by the above-described cyclization which is carried out under basic conditions, the desired salts of the compounds of formula I in which $R^1$ or $R^2$ signifies hydrogen can also be manufactured from these compounds I in a manner known per se such as, for example, by dissolving the compound of formula I in a solution of a respective inorganic or organic base. The salt formation is generally effected within a short time at room temperature. In one embodiment the sodium salt is manufactured by dissolving the uracil derivative I in aqueous sodium hydroxide solution at room temperature, with equivalent amounts of the uracil derivative and of sodium hydroxide being used. The solid salt can then be isolated by precipirarion with a suitable inert solvent or by evaporation of the solvent. A further embodiment comprises introducing an aqueous solution of an alkali metal salt of the uracil derivative I into an aqueous solution of a salt which has a metal ion other than an alkali metal ion, whereby the second metal salt of the uracil derivative is manufactured. This embodiment generally serves for the manufacture of uracil metal salts which are insoluble in water.

The compounds of formula I, enol ethers as well as salts which are obtained can be isolated and purified according to methods known per se. Further, the sequence in which possible combinations of process variants (b) to (f) are conveniently carrried out in order to avoid possible undesired concurrent reactions is familiar to the person skilled in the art.

Insofar as no planned synthesis for the isolation of pure isomers is carried out, the product can result as a mixture of two or more isomers. The isomers can be separated according to methods known per se. If desired, pure optically active isomers can also be manufactured, for example, by synthesis from corresponding optically active starting materials.

The starting materials of formula II, which are novel, can be produced in a manner known per, e.g. in accordance with the following Reaction Schemes [methods (aa), (bb) and (cc)]:

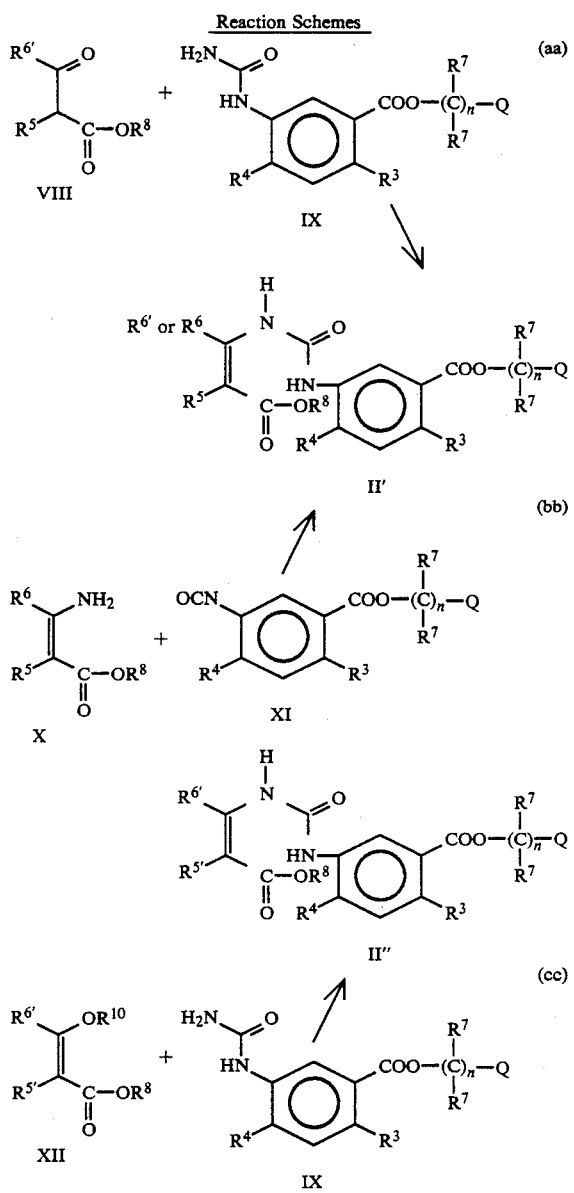

In the above Reaction Scheme $R^3$, $R^4$, $R^5$, $R^6$, $R^7$, $R^8$, n and Q have the significances given above; $R^{5'}$ signifies hydrogen or $C_{1-4}$-alkyl; $R^{6'}$ signifies $C_{1-4}$-alkyl; and $R^{10}$ signifies lower alkyl, preferably $C_{1-4}$-alkyl.

Method (aa) is conveniently carried out by reacting the compounds of formulae VIII and IX with each other in an essentially anhydrous diluent and in the presence of an acidic catalyst at an elevated temperature. As diluents there come into consideration especially organic solvents which form azeotropes with water, such as aromatics, e.g. benzene, toluene and xylenes; halogenated hydrocarbons such as methylene chloride, chloroform, carbon tetrachloride and chlorobenzene; and aliphatic and cyclic ethers such as 1,2-dimethoxyethane, tetrahydrofuran and dioxan, and as acidic catalysts there especially come into consideration strong mineral acids such as sulphuric acid and hydrochloric acid; organic acids such as p-toluenesulphonic acid; phosphorus-containing acids such as orthophosphoric acid and polyphosphoric acid; and acidic cation exchangers such as "Amberlyst 15" (Fluka). The reaction is generally carried out in a temperature range of about 70° C. to 120° C., preferably at the reflux temperature of the reaction mixture. Under these reaction conditions the desired rapid removal of the water which is formed in the reaction is achieved.

The reaction according to method (bb) is conveniently effected in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon. e.g. n-hexane, benzene, toluene or a xylene; or a halogenated, aliphatic hydrocarbon, e.g. methylene chloride, chloroform, carbon tetrachloride or 1,2-dichloroethane, as well as optionally in the presence of a base, especially an organic tertiary base such as triethylamine or pyridine, whereby the latter can serve not only as the solvent but also as the base, or a metal hydride such as sodium hydride or potassium hydride. The reaction temperatures are preferably in the range of about −80° C. to 50° C., with the reaction being carried out particularly at temperatures between −30° C. and room temperature.

The reaction according to method (cc) is conveniently carried out in an inert, water-miscible, organic solvent such as an aliphatic or cyclic ether, e.g. 1,2-dimethoxyethane, tetrahydrofuran or dioxan, or a lower alkanol such as ethanol at temperatures between 50° C. and 100° C. preferably at the reflux temperature of the reaction mixture, or in an aromatic solvent such as benzene toluene or a xylene in the presence of an acidic catalyst such as hydrochloric acid or p-toluenesulphonic acid at temperatures between 50° C. and 100° C. preferably 60° C. to 80° C.

The starting materials of formulae III and V and their production are for the most part described in European Patent Publication No. 195,346. Those starting materials III and V whose manufacture is not described can be produced analogously to the known starting materials. The reactive derivatives of the benzoic acids of formula III, which can likewise be used as starting materials, can be produced from these benzoic acids according to methods known per se. On the other hand all enol ethers of the benzoic acids III, i.e. the compounds of the general formula

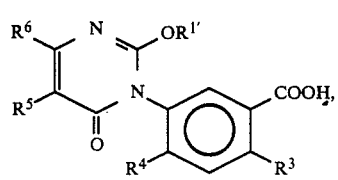

which can likewise be used as starting materials in process variant (c), are novel. These can be produced, for example, in accordance with the following Reaction Scheme in which $R^3$, $R^4$, $R^5$, $R^6$, $R^{1'}$, $R^9$, Hal and $M^\oplus$ have the significances given above:

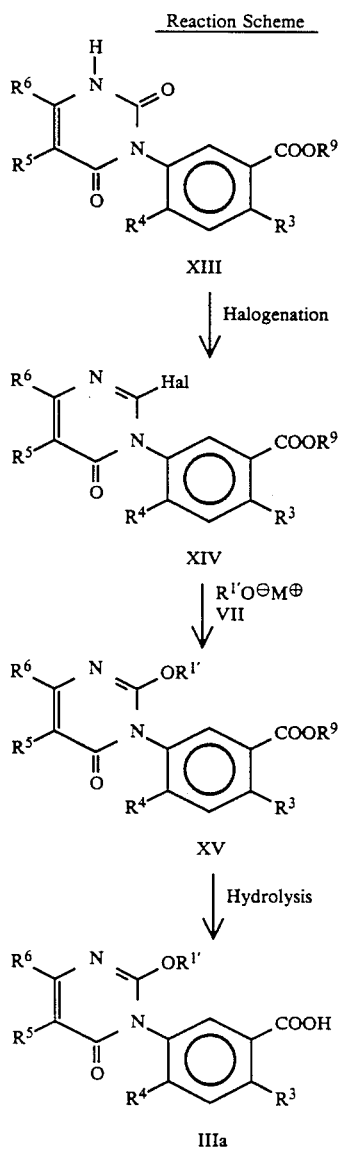

Reaction Scheme

In the halogenation of the benzoic acid ester of formula XIII there is used as the halogenating agent especially thionyl chloride, phosphorus pentachloride or phosphorus oxychloride or phosphorus pentabromide or phosphoryl bromide. If desired, a mixture of phosphorus pentachloride and phosphorus oxychloride or of phosphorus pentabromide and phosphoryl bromide is used, in which case an excess of phosphorus oxychloride or phosphoryl bromide can serve as the diluent. The chlorination or bromination can be carried out in the presence of an inert diluent, especially an aprotic organic solvent such as an aliphatic or aromatic hydrocarbon, e.g. n-hexane, benzene, toluene or a xylene; a halogenated aliphatic hydrocarbon, e.g. methylene chloride, chloroform or 1,2-dichloroethane; a halogenated aromatic hydrocarbon, e.g. chlorobenzene, or a tertiary amine, e.g. N,N-dimethylaniline, but this is not necessary where phosphorus oxychloride or phosphoryl bromide is used as the halogenating agent. When thionyl chloride is used as the halogenating agent it has been found to be convenient to add a catalytic amount of dimethylformamide. The reaction temperatures generally lie between 0° C. and the reflux temperature of the reaction mixture, preferably between 80° C. and 120° C.

The reaction of the compound XIV with the compound VII can be effected analogously to process variant f) described above.

The subsequent hydrolysis of compound XV can be carried out according to methods known per se, especially using an inorganic acid and optionally in the presence of an organic solvent and/or of water. As acids there preferably come into consideration hydrochloric acid, sulphuric acid and phosphoric acid, as organic solvents there preferably come into consideration alcohols, e.g. ethanol; aliphatic or cyclic ethers, e.g. 1,2-dimethoxyethane, tetrahydrofuran and dioxan, and optionally chlorinated aliphatic or alicyclic hydrocarbons. e.g. methylene chloride, tetrachloromethane, n-hexane and cyclohexane. The reaction temperatures generally lie between −20° C. and 120° C., preferably between 0° C. and 30° C. especially between 15° C. and 20° C.

The reactive derivatives of the enol ethers of the benzoic acids III, which can also be used as starting materials, can be produced from these enol ethers according to methods known per se.

The starting materials of formula VI used in process variant f) can be produced by halogenating the corresponding uracil derivatives of formula I' given above analogously to the above-described process XIII→XIV (see the Reaction Scheme and the description of the reaction conditions following therefrom).

The uracil derivatives of formula I' and I" which serve as starting materials in process variants (b) and (e) are sub-groups of compounds of formula I. The remaining starting materials and reagents which are involved in process variants (c), (d) and (f) as well as in the Reaction Schemes are either known or can be produced according to methods known per se.

The compounds of formula I as well as their enol ethers or salts possess herbicidal properties and are suitable for the control of weeds, including weed grasses, especially *Setaria faberii, Digitaria sanguinalis, Poa annua, Chenopodium album, Amaranthus retroflexus, Abutilon theophriasti, Sinapsis alba* and *Datura stramonium*, in diverse crop cultivations, especially in cereal, soya, maize, rice and cotton cultivations. Moreover, the compounds are not only pre-emergence, but also post-emergence herbicides.

The compounds of formulae IIIa as well as their salts also possess herbicidal properties and can be used for the control of weed grasses and weeds especially the aforementioned, in a similar manner to the compounds I. The novel compounds IIIa as well as their salts, weed control compositions which contain these compounds as active substances, the above-defined process for the production of these compounds and the use of these compounds or compositions for the control of weeds form further objects of the present invention. The salts of the compounds IIIa are especially alkali metal salts, alkaline earth metal salts, ammonium salts and salts with organic bases such as are described above in more detail in connection with the compounds I. The compounds IIIa can be converted into their salts just like the compounds I. Hereinafter, the compounds of formula I and their enol ethers or salts as well as the compounds of formulae IIIa and their salts are denoted collectively as compounds in accordance with the invention.

In practice, a concentration of 1 g to 3 kg of compound in accordance with the invention/ha, preferably 10 to 500 g of compound in accordance with the invention/ha, is usually sufficient to achieve the desired herbicidal effect. The concentration range 15 to 100 g of compound in accordance with the invention/ha is especially preferred.

The weed control composition in accordance with the invention is characterized in that it contains an effective amount of at least one compound of formula I, as defined above, or of an enol ether or salt thereof or of a compound of formula IIIa or of a salt thereof as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants these compounds, namely the herbicidally active substances can be converted into the usual formulations such as dusts. Powders, granulates, solutions, emulsions, suspensions, emulsifiable concentrates, pastes and the like.

The compounds of formula I. their enol ethers and the compounds of formulae IIIa are generally insoluble in water, whereas the salts, especially the alkali metal salts and ammonium salts, are generally soluble in water, and can be formulated according to methods which are usual for water-insoluble or water-soluble compounds using the respective formulation adjuvants. The manufacture of the compositions can be carried out in a manner known per se, e.g. by mixing the particular active substance with solid carrier substances, by dissolution or suspension in suitable solvents or dispersion media, if necessary using tensides as wetting or emulsifying agents and/or dispersing agents, by diluting preprepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc. attapulgite and montmorillonite); synthetic mineral substances such as highly dispersible silicic acid, aluminium oxide and silicates; organic substances such as cellulose, starch urea and synthetic resins; and fertilizers such as phosphates and nitrates, whereby such carrier substances can be present e.g. as powders or as granulates.

As solvents or dispersion media there essentially come into consideration: aromatics such as benzene toluene, xylenes and alkylnaphthalene; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide. N-methylpyrrolidone and dimethyl sulphoxide, such solvents preferably having flash points of at least 30° C. and boiling points of at least 50° C. and water. Among the solvents or dispersion media there also come into consideration so-called liquified gaseous extenders or carrier substances which are those products which are gaseous at room temperature and under normal pressure. Examples of such products are especially aerosol propellants such as halogenated hydrocarbons, e.g. dichlorodifluoromethane. If the weed control composition in accordance with the invention is present in the form of a pressurized pack, then a solvent is conveniently used in addition to the propellant.

The tensides (wetting and emulsifying agents) can be non-ionic compounds such as condensation products of fatty acids fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonates of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents. e.g. epichlorohydrin, phenyl glycidyl ether and soya epoxides; antioxidants, e.g. gallic acid esters and butylhydroxytoluene; UV-absorbers, e.g. substituted benzophenones diphenylacrylonitrile acid esters and cinnamic acid esters; and deactivators, e.g. salts of ethylenediaminotetraacetic acid and polyglycols.

The weed control compositions in accordance with the invention can contain, in addition to the active substances in accordance with the invention, synergists and other active substances, e.g. insecticides, acaricides, fungicides, plant growth regulators and fertilizers. Such combination compositions are suitable for intensifying the activity or for broadening the spectrum of activity The weed control compositions in accordance with the invention generally contain between 0.001 and 95 weight percent, preferably between 0.5 and 75 weight percent, of one or more compounds in accordance with the invention as the active substance(s). They can be present e.g. in a form which is suitable for storage and transport. In such formulations. e.g. emulsifiable concentrates, the active substance concentration is normally in the higher range, preferably between 1 and 50 weight percent, especially between 10 and 30 weight percent. These formulations can then be diluted, e.g.

with the same or different inert substances, to give active substance concentrations which are suitable for practical use, i.e. preferably about 0.001 to 10 weight percent, especially about 0.005 to 5 weight percent. The active substance concentrations can, however, also be smaller or greater.

As mentioned above, the manufacture of the weed control compositions in accordance with the invention can be carried out in a manner known per se.

For the manufacture of pulverous preparations the active substance, i.e. at least one compound of in accordance with the invention, can be mixed with a solid carrier substance, e.g. by grinding together; or the solid carrier substance can be impregnated with a solution or suspension of the active substance and then the solvent or dispersion medium can be removed by evaporation, heating or sucking-off under reduced pressure. By adding tensides or dispersing agents such pulverous preparations can be made readily wettable with water, so that they can be converted into aqueous suspensions which are suitable e.g. as spay compositions.

The active substance can also be mixed with a tenside and a solid carrier substance to form a wettable powder which is dispersible in water, or it can be mixed with a solid pre-granulated carrier substance to form a product in the form of a granulate.

When desired, the active substance can be dissolved in a water-immiscible solvent such as, for example, a high-boiling hydrocarbon, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention which forms a further object of the present invention, can be carried out according to usual application methods such as sprinkling, spraying, dusting, watering or scattering. The method in accordance with the invention for the control of weeds is characterized by treating the locus to be protected against weeds and/or the weeds with a compound in accordance with the invention or with a weed control composition in accordance with the invention.

The following Examples serve to illustrate the invention in more detail.

I. Manufacture of the compounds of formula I:

EXAMPLE 1

3.0 g of 2-chloro-5-[3,6-dihydro-2,6-dioxo-3-methyl-4-trifluoromethyl-1(2H)-pyrimidinyl]-4-fluorobenzoic acid are heated at reflux temperature for 3 hours in 20 ml of benzene and 2.9 ml of thionyl chloride together with 2 drops of dimethylformamide. The reaction mixture is subsequently evaporated to dryness and dissolved in 20 ml of dioxan. This solution, which consists mainly of the acid chloride of the above-mentioned benzoic acid and the solvent, is added dropwise to a solution of 0.86 g of 3-thietanol and 1.0 g of pyridine in 10 ml of dioxan. The reaction mixture is then stirred at room temperature for 2.5 hours, treated with 400 ml of water and extracted twice with 400 ml of ethyl acetate each time. The combined organic phases are washed twice with 200 ml of 1N hydrochloric acid each time and once with 200 ml of saturated sodium chloride solution, dried over anhydrous sodium sulphate and evaporated. The residue is purified by chromatography on silica gel with ethyl acetate/n-hexane (2:3). In this manner there is obtained thietan-3-yl 2-chloro-5-[3,6-dihydro-2 6-dioxo-3-methyl-4-trifluoromethyl-1(2H)-pyrimidinyl]-4-fluorobenzoate which can be recrystalized from ethyl acetate/n-hexane; m.p. 121°-123° C.

In an analogous manner, starting from 2-chloro-5-[3,6-dihydro-2,6-dioxo-3-methyl-4-trifluoromethyl-1(2H)-pyrimidinyl]-4-fluorobenzoic acid via its acid chloride and:

cycloheptanol there is obtained cycloheptyl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO. 400 MHz): 1.40–1.82 (m,10H), 1.94–2.04 (m.2H), 3.41 (s,3H), 5.07–5.16 (m,1H), 6.61 (s,1H), 7.87 (d,1H), 8.00 (d,1H);

3-hydroxytetrahydrofuran there is obtained tetrahydrofuran-3-yl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO, 400 MHz): 2.01–2.10 (m,1H), 2.20–2.31 (m,1H), 3.42 (s,3H), 3.73–3.80 (m,1H), 3.82–3.91 (m,3H), 5.48–5.53 (m,1H), 6.62 (s,1H), 7.89 (d,1H), 8.07 (d,1H);

5-hydroxy-1,3-dioxane there is obtained 1,3-dioxan-5-yl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO, 400 MHz): 3.42 (s,3H), 3.97–4.02 (m,2H), 4.05–4.11 (m,2H), 4.78 (d,1H), 4.88–4.93 (m,2H), 6.62 (s,1H), 7.92 (d,1H), 8.08 (d,1H);

cyclopropylmethanol there is obtained cyclopropylmethyl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO, 400 MHz): 0.34–0.39 (m,2H), 0.54–0.60 (m,2H), 1.16–1.24 (m,1H), 3.42 (s,3H), 4.15 (d,2H), 6.61 (s,1H), 7.90 (d,1H), 8.05 (d,1H);

3-hydroxymethyl-3-methyl-oxetane there is obtained (3-methyl-3 oxetanyl)methyl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO, 400 MHz): 1.35 (s,3H), 3.42 (s,3H), 4.30 (d,2H), 4.44 (s,2H), 4.48 (d,2H), 6.62 (s,1H), 7.90 (d,1H), 8.07 (d,1H);

2-tetrahydrofurylmethanol there is obtained tetrahydrofurfuryl 2-chloro-5-[3,6-dihydro-2,6-dioxo-3 methyl-4-trifluoromethyl-1(2H)-pyrimidinyl]-4-fluorobenzoate as an oil, $^1$H-NMR ($D_6$-DMSO, 400 MHz): 1.59–1.70 (m,1H), 1.76–1.90 (m,2H), 1.93–2.04 (m,1H), 3.42 (s,3H), 3.62–3.69 (m,1H), 3.72–3.80 (m,1H), 4.11–4.17 (m,1H), 4.21–4.33 (m,2H), 6.61 (s,1H), 7.90 (d,1H), 8.05 (d,1H);

4-hydroxymethyl-1,3-dioxolane there is obtained (1,3-dioxolan-4-yl)methyl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO, 400 MHz): 3.42 (s.3H), 3.67–3.72 (m,1H), 3.96–4.04 (m,1H), 4.32–4.42 (m,3H), 4.83 (s,1H), 4.94 (s,1H), 6.62 (s,1H), 7.91 (d,1H), 8.08 (d,1H);

benzyl alcohol there is obtained benzyl 2-chloro-5-[3,6-dihydro-2,6-dioxo-3-methyl-4-trifluoromethyl-1(2H)-pyrimidinyl]-4-fluorobenzoate as an oil, $^1$H-NMR ($D_6$-DMSO. 400 MHz): 3.40 (s,3H), 5.37 (s,2H), 6.60 (s,1H), 7.36–7.43 (m,3H), 7.47–7.50 (m,2H), 7.90 (d,1H), 8.08 (d,1H);

R-4,4-dimethyl-3-hydroxy-2-oxo-tetrahydrofuran there is obtained 4,4-dimethyl-2-oxo-tetrahydrofuran-3-yl R-2-chloro-5-[3,6-dihydro-2,6-dioxo-3-methyl-4-trifluoromethyl-1(2H)-pyrimidinyl]-4-fluorobenzoate as an oil, $[\alpha]_D^{20} = -10.6°$; $^1$H-NMR (D6-DMSO, 400 MHz): 1.11 (s,3H), 1.22 (s,3H), 3.43 (s,3H), 4.13 (d,1H), 4.24 (d,1H), 5.89 (s,1H), 6.62 (d,1H), 7.96 (d,1H), 8.15 (d,1H);

4-hydroxy-2,2,6,6-tetramethyl-tetrahydrothiopyran there is obtained 2,2,6,6-tetramethyl-tetrahydrothiopyran-4-yl 2-chloro-5-[3,6-dihydro-2,6-dioxo-3-methyl-4-trifluoromethyl-1(2H)-pyrimidinyl]-4-fluorobenzoate as an oil, $^1$H-NMR (D6-DMSO, 400 MHz): 1.25 (s,6H), 1.49 (s,6H), 1.61 (t,2H), 2.19 (dd,2H), 3.42 (s,3H), 5.31–5.38 (m,1H), 6.62 (s,1H), 7.89 (d,1H), 8.06 (d,1H);

cyclopentanol there is obtained cyclopentyl 2-chloro-5-[3,6-dihydro-2,6-dioxo-3-methyl-4-trifluoromethyl-1(2H)-pyrimidinyl]-4-fluorobenzoate as an oil, $^1$H-NMR (D6-DMSO. 400 MHz): 1.50–2.00 (m,8H), 3.42 (s,3H), 5.31–5.38 (m,1H), 6.61 (s,1H), 7.87 (d,1H), 8.02 (d,1H);

phenol there is obtained phenyl 2-chloro-5-[3,6-dihydro-2,6-dioxo-3-methyl-4-trifluoromethyl-1(2H)-pyrimidinyl]-4-fluorobenzoate as an oil, $^1$H-NMR (D6-DMSO, 400 MHz): 3.43 (s,3H). 6.63 (s,1H), 7.30–7.37 (m,3H), 7.45–7.53 (m,2H), 7.99 (d,1H), 8.39 (d,1H);

2-cyclohexylethanol there is obtained 2-cyclohexylethyl 2-chloro-5-[3,6-dihydro-2,6-dioxo-3-methyl-4-trifluoromethyl-1(2H)-pyrimidinyl]-4-fluorobenzoate as an oil, $^1$H-NMR (D6-DMSO, 400 MHz): 0.87–0.98 (m,2H), 1.10–1.25 (m.3H), 1.32–1.45 (m,1H), 1.56–1.75 (m,7H), 3.42 (s,3H), 4.34 (t,2H), 6.61 (s,1H), 7.89 (d,1H), 8.03 (d,1H);

1-cyclopropylethanol there is obtained 1-cyclopropylethyl 2-chloro-5-[3,6-dihydro-2,6-dioxo-3-methyl-4-trifluoromethyl-1(2H)-pyrimidinyl]-4-fluorobenzoate as an oil, $^1$H-NMR (D6-DMSO, 400 MHz): 0.34–0.45 (m,2H), 0.47–0.60 (m,2H), 1.08–1.18 (m,1H), 1.38 (d,3H), 3.43 (s,3H), 4.55 (m.1H), 6.61 (s,1H), 7.88 (d,1H), 8.01 (d,1H), mass spectrum (m/e): M+434(4);

p-methoxyphenol there is obtained p-methoxyphenyl 2-chloro-5-[3,6-dihydro-2,6-dioxo-3-methyl-4-trifluoromethyl-1(2H)-pyrimidinyl]-4-fluorobenzoate, m.p. 128°–129° C., mass spectrum (m/e): M+472(24);

5-hydroxy-1,3-benzodioxol there is obtained 1,3-benzodioxol-5-yl 2-chloro-5-[3,6-dihydro-2,6 dioxo-3-methyl-4-trifluoromethyl-1(2H)-pyrimidinyl]-4-fluorobenzoate, m.p. 134°–135° C., mass spectrum (m/e): M+486(15);

2,4-dichlorobenzyl alcohol there is obtained 2,4-dichlorobenzyl 2-chloro-5-[3,6-dihydro-2,6-dioxo-3-methyl-4-trifluoromethyl-1(2H)-pyrimidinyl]-4-fluorobenzoate, m.p. 88°–90° C.;

3-nitrobenzyl alcohol there is obtained 3-nitrophenyl-chloro-5-[3,6-dihydro-2,6-dioxo-3-methyl-4-trifluoromethyl-1(2H)-pyrimidinyl]-4-fluorobenzoate, $^1$H-NMR (D6-DMSO, 400 MHz): 3.41 (s,3H), 5.52 (s,2H), 6.60 (s,1H), 7.70–7.74 (m,1H), 7.92 (d,1H), 7.95–7.98 (m,1H), 8.12 (d,1H), 8.20–8.26 (m.1H), 8.37–8,39 (m,1H) mass spectrum (m/e): M+501(3);

cyclohexanol there is obtained cyclohexyl 2-chloro-5-[3,6-dihydro-2,6-dioxo-3-methyl-4-trifluoromethyl-1(2H)-pyrimidinyl]-4-fluorobenzoate, $^1$H-NMR (D6-DMSO, 400 MHZ): 1.27–1.59 (m,6H), 1.66–1.76 (m,2H), 1.86–1.96 (m,2H), 3.39 (s,3H), 4.93–5.00 (m,1H), 6.61 (s,1H), 7.87 (d,1H), 8.01 (d,1H); mass spectrum: (m/e): M+448(1);

3.5-bis-(trifluoromethyl)benzyl alcohol there is obtained 3,5-bis(trifluoromethyl)phenyl 2-chloro-5-[3,6-dihydro-2,6-dioxo-3-methyl-4-trifluoromethyl-1(2H)-pyrimidinyl]-4-fluorobenzoate, m.p. 129°–130° C.;

p-cyanophenol there is obtained p-cyanophenyl 2-chloro-5-[3,6-dihydro-2,6-dioxo-3-methyl-4-trifluoromethyl-1(2H)-pyrimidinyl]-4-fluorbenzoate, $^1$H-NMR (D6-DMSO, 400 MHz): 3.43 (s,3H), 6.63 (s,1H), 7.57–7.61 (m,2H), 7.98–8.02 (m,3H), 8.42 (d,1H);

tetrahydrothiophen-3-ol there is obtained tetrahydrothien-3-yl 2-chloro-5-[3,6-dihydro-2.6-dioxo-3-methyl-4-trifluoromethyl-1(2H)-pyrimidinyl]-4-fluorobenzoate, $^1$H-NMR (D6-DMSO, 400 MHz): 1.98–2.09 (m,1H) 2.28–2.38 (m,1H), 2.91–3.00 (m,3H), 3.18–3.24 (m,1H), 3.42 (s.3H), 5.66–5.73 (m,1H), 6.62 (s,1H), 7.89 (d,1H), 8.03 (d,1H);

tetrahydropyran-4-ol there is obtained tetrahydropyran-3-yl 2-chloro-5-chloro-5-[3,6-dihydro-2,6-dioxo-3-methyl-4-trifluoromethyl-1(2H)-pyrimidinyl]-4-fluorobenzoate. m.p. 173°–174° C.

2,2-dimethyl-4-hydroxymethyl-1,3-dioxolane there is obtained (2,2-dimethyl-1,3-dioxolan-4-yl)methyl 2-chloro-5-[3,6-dihydro-2,6-dioxo-3-methyl-4-trifluoromethyl-1(2H)-pyrimidinyl]-4-fluorobenzoate, $^1$H-NMR (D6-DMSO, 400 MHz): 1.28 (s,3H), 1.33 (s,3H), 3.42 (s,3H), 3.75–3.80 (m,1H), 4.02–4.10 (m.1H), 4.25–4.43 (m,3H), 6.61 (s,1H), 7.90 (d,1H), 8.07 (d,1H);

In an analogous manner, starting from 2-chloro-5-[3,6-dihydro-2,6-dioxo-3-methyl-4-trifluoromethyl-1(2H)-pyrimidinyl]-benzoic acid via its acid chloride and 1-cyclopropylethanol there is obtained 1-cyclopropylethyl 2-chloro-5-[3,6-dihydro-2,6-dioxo-3-methyl-4-trifluoromethyl-1(2H)-pyrimidinyl]-benzoate, m.p. 118°–119° C.;

In an analogous manner, starting from 2-chloro-5-[3,6-dihydro-2,6-dioxo-3-methyl-4-pentafluoroethyl-1(2H)-pyrimidinyl]-4-fluorobenzoic acid via its acid chloride and tetrahydrofuran-3-ol there is obtained 3-tetrahydrofuryl 2-chloro-5-[3,6-dihydro-2,6-dioxo-3-methyl-4-pentafluoroethyl-1(2H)-pyrimidinyl]-4-fluorobenzoate, $^1$H-NMR (D6-DMSO, 400 MHz): 2.00–2.09 (m, 1H), 2.20–2.32 (m,1H), 3.43 (s,3H), 3.74–3.92 (m,4H), 5.48–5.56 (m,1H), 6.50 (s,1H), 7.89 (d,1H), 8.08 (d,1H);

In an analogous manner, starting from 2-chloro-5-[3,6-dihydro-3,4-dimethyl-2,6-dioxo-1(2H)-pyrimidinyl]-4-fluorobenzoic acid and hydroxymethylcyclopropane there is obtained cyclopropylmethyl 2-chloro 5-[3,6-dihydro-3,4-dimethyl-2,6-dioxo-1(2H)-pyrimidinyl]-4-fluorobenzoate, $^1$H-NMR (CDCl3, 400 MHz): 0.31–0.38 (m,2H), 0.57–0.64 (m,2H), 1.18–1.27 (m,1H), 2.32 (s,3H), 3.45 (s,3H), 4.11–4.15 (m,2H), 5.74 (s.1H), 7.35 (d,1H). 7.89 (d,1H); mass spectrum (m/e): M+366(13);

3-hydroxytetrahydrofuran there is obtained 3-tetrahydrofuryl 2-chloro-5-[3,6-dihydro-3,4-dimethyl-2,6-dioxo-1(2H)-pyrimidinyl]-4-fluorobenzoate, m.p. 149°–151° C.;

1-cyclopropylethanol there is obtained 1-cyclopropylethyl 2-chloro-5-[3,6-dihydro-3,4-dimethyl-2,6-dioxo-1(2H)-pyrimidinyl]-4-fluorobenzoate as an oil, $^1$H-NMR (D6-DMSO, 400 MHz): 0.33–0.43 (m,2H), 0.47–0.58 (m,2H), 1.07–1.17 (m,1H), 1.37 (d,3H), 2.33 (s,3H), 3.35 (s,3H), 4.49–4.57 (m,1H), 5.81 (s,1H), 7.82 (d,1H), 7.91 (d,1H); mass spectrum (m/e): M+380(8);

cyclopentanol there is obtained cyclopentyl 2-chloro-5-[3,6-dihydro-3,4-dimethyl-2,6-dioxo-1(2H)-pyrimidinyl]-4-fluorobenzoate as an oil, $^1$H-NMR (D6-

DMSO, 400 MHz): 1.58–1.97 (m,8H), 2.33 (s,3H), 3.35 (s,3H), 5.31–5.36 (m,1H), 5.80 (s,1H), 7.81 (d,1H), 7,91 (d,1H); mass spectrum (m/e): M+380(19);

EXAMPLE 2

3.4 g of 2-chloro-4-fluoro-5-[2-methoxy-6-oxo-4-trifluoromethyl-1(6H) pyrimidinyl]-benzoic acid are heated at reflux temperature for 3 hours in 25 ml of benzene and 3.4 ml of thionyl chloride together with 2 drops of dimethylformamide. The reaction mixture is subsequently evaporated to dryness and dissolved in 20 ml of dioxan. This solution, which consists mainly of the acid chloride of the above-mentioned benzoic acid and the solvent, is added dropwise to a solution of 1.0 g of 3-thietanol and 1.3 g of pyridine in 20 ml of dioxan. The reaction mixture is then stirred at room temperature for 3.5 hours, treated with 400 ml of water and extracted twice with 400 ml of ethyl acetate each time. The combined organic phases are washed twice with 200 ml of 1N hydrochloric acid each time and once with 200 ml of saturated sodium chloride solution, dried over anhydrous magnesium sulphate and evaporated. The residue is purified by chromatography on silica gel with diethyl ether/n-hexane (1:2). In this manner there is obtained thietan-3-yl 2-chloro-4-fluoro-5-[2-methoxy-6-oxo-4-trifluoromethyl-1(6H)-pyrimidinyl]-benzoate as a colourless oil, $^1$H-NMR(CDCl$_3$, 400 MHz): 3.37–3.44 (m,2H), 3.57–3.66 (m,2H), 4.03 (s,3H), 5.85 (quintet, 1H), 6.63 (s,1H), 7.42 (d,1H), 7.88 (d,1H).

In an analogous manner, from 2-chloro-4-fluoro-5-[2-methoxy-6-oxo-4-trifluoromethyl-1(6H)-pyrimidinyl]-benzoic acid via its acid chloride and tetrahydrofuran-3-ol there is obtained 3-tetrahydrofuryl 2-chloro-4-fluoro-5-[2-methoxy-6-oxo-4-trifluoromethyl-1(6H)-pyrimidinyl]-benzoate, $^1$H-NMR (D$_6$-DMSO, 400 MHz): 2.02–2.10 (m,1H), 2.20–2.30 (m,1H), 3.75–3.92 (m,4H), 3.96 (s,3H), 5.48–5.55 (m,1H), 6.86 (s,1H), 7.95 (d,1H), 8.25 (d,1H), mass spectrum (m/e): M+436(2).

EXAMPLE 3

3.0 g of potassium 2-chloro-4-fluoro-5-[3,6-dihydro-2,6-dioxo-3-methyl-4-trifluoromethyl-1(2H)-pyrimidinyl]-4-fluorobenzoate and 0.6 ml of epichlorohydrin are heated at 70° C. for 3 hours in 25 ml of dimethylformamide. Thereafter, the reaction solution is added to 500 ml of water and adjusted to pH 10 to 11 with a small amount of saturated potassium carbonate solution. It is extracted twice with 300 ml of ethyl acetate. The organic phases are washed twice with 200 ml of water, dried over anhydrous magnesium sulphate and concentrated. The residue is purified by chromatography on silica gel with ethyl acetate/n-hexane. There is obtained 2,3-epoxypropyl 2-chloro-5-[3,6-dihydro-2,6-dioxo-3-methyl-4 -trifluoromethyl-1(2H)-pyrimidinyl]-4-fluorobenzoate as a pale yellow oil, $^1$H-NMR(D$_6$-DMSO, 400 MHz): 2.73 (m,1H), 2.85 (m,1H), 32 (m,1H), 3.42 (s,3H), 4.10 (m,1H), 4.69 (m,1H), 6.62 (s,1H), 7.92 (d,1H), 8.11 (d,1H), mass spectrum (m/e): M+422(16).

EXAMPLE 4

103 g of chlorodifluoromethane are conducted into a suspension of 145.0 g of isopropyl 2-chloro-4-fluoro-5-[3,6-dihydro-2,6-dioxo-4-methyl-1(2H)-pyrimidinyl]-benzoate and 59.0 g of anhydrous, finely powdered potassium carbonate in 1 l of dimethylformamide for 6 hours while stirring at 80° C. After cooling the solid constituent is filtered off under suction and rinsed with 100 ml of dimethylformamide. The filtrate is concentrated to a large extent under reduced pressure at 55° C., the residue is poured into 2 l of water and the aqueous mixture is adjusted to pH 3 with concentrated hydrochloric acid. The mixture is extracted with 1.5 l of ethyl acetate and the organic phase is washed twice with 1 l of water each time. dried over anhydrous sodium sulphate and evaporated to dryness under reduced pressure. The resinous residue is purified by chromatography on a silica gel column using ethyl acetate/n-hexane (1:1) as the eluent. The product is dissolved in 1500 ml of hot n-hexane and the solution is treated with charcoal, filtered and concentrated to 700 ml at an elevated temperature. It is subsequently seeded and cooled to 5° C. while stirring. The resulting crystals are filtered off under suction, washed with n-hexane and dried. There is obtained isopropyl 2-chloro-5-[3-difluoromethyl-3,6-dihydro-2,6-dioxo-4-methyl-1(2H)-pyrimidinyl]-4-fluorobenzoate, m.p. 90°–93° C.

EXAMPLE 5–8

The corresponding uracil derivative of formula II is alkylated with chlorodifluoromethane analogously to the procedure described in Example 4 in order to manufacture the compounds of formula I listed in the following Table 1.

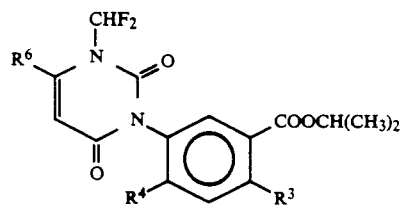

TABLE 1

| Example | R$^3$ | R$^4$ | R$^6$ | Physical data |
|---|---|---|---|---|
| 5 | Cl | F | C$_2$H$_5$ | $^1$H-NMR (CDCl$_3$, 400 MHz): 7.83 ppm (d,1H), 7.74 ppm (t,1H), 7.36 ppm (d,1H), 5.90 ppm (s,1H), 5.25 ppm (m,1H), 2.87 ppm (q,2H), 1.36 ppm (d,6H), 1.31 ppm (t,3H). |
| 6 | Br | F | C$_2$H$_5$ | $^1$H-NMR (CDCl$_3$, 400 MHz): 7.81 ppm (d,1H), 7.74 ppm (t,1H), 7.57 ppm (d,1H), 5.90 ppm (s,1H), 5.24 ppm (m,1H), 2.87 ppm (q,2H), 1.37 ppm (d,6H), 1.32 ppm (t,3H). |
| 7 | Br | F | CH$_3$ | $^1$H-NMR (CDCl$_3$, 400 MHz): 7.80 ppm (d,1H), 7.72 ppm (t,1H), 7.57 ppm (d,1H), 5.83 ppm (s,1H), 5.24 ppm (m,1H), 2.49 pp (d,3H), 1.37 ppm (d,6H). |
| 8 | Cl | H | CH$_3$ | m.p. 115–117° C. |

EXAMPLE 9

A suspension of 2.00 g of 2-chloro-5-[3-difluoromethyl-3,6-dihydro-2,6-dioxo-4-methyl -1(2H)-pyrimidinyl]-4-fluorobenzoic acid, 1.63 g of methyl iodide and 0.61 g of sodium carbonate in 20 ml of acetone is heated at the boiling point for 4 hours. Subsequently, 1.63 g of methyl iodide are added and, after 2 hours, a further 1.63 g. The reaction mixture is heated at reflux temperature for a further 16 hours. After cooling insoluble constituents are filtered off under suction and rinsed with acetone. and the filtrate is evaporated to dryness under reduced pressure. The residue is dissolved in 100 ml of ethyl acetate and the solution is washed twice with 100 ml of water each time. The organic phase is dried over anhydrous sodium sulphate and evaporated to dryness. The resinous residue is purified by chromatography on a silica gel column using diethyl ether/n-hexane (1:2) as the eluent. The product is recrystallized from diethyl ether/n-hexane. There is obtained methyl 2-chloro-5-[3-difluoro-methyl-3,6-dihydro-2,6-dioxo-4-methyl -1(2H)-pyrimidinyl]-4-fluorobenzoate, m.p. 121°–123° C.

EXAMPLES 10–19

2-Chloro-5-[3-difluoromethyl-3,6-dihydro-2,6-dioxo-4-methyl-1(2H)-pyrimidinyl]-4-fluorobenzoic acid is appropriately esterified analogously to the procedure described in Example 9 in order to manufacture the compounds of formula I listed in the following Table 2.

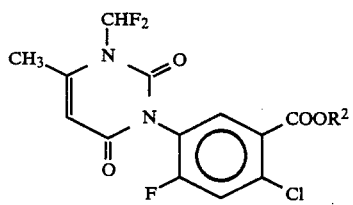

TABLE 2

| Example | R² | Physical data |
|---|---|---|
| 10 | $C_2H_5$ | M.p. 90–92° C. |
| 11 | $nC_3H_7$ | ¹H-NMR (CDCl₃, 400 MHz): 1.01 (t,3H), 1.77 (m,2H), 2.49 (s,3H), 4.28 (t,2H), 5.83 (s,1H), 7.37 (d,1H), 7.72 (t,1H), 7.87 (d,1H). |
| 12 | $nC_4H_9$ | ¹H-NMR (CDCl₃, 400 MHz): 0.96 (t,3H), 1.44 (m,2H), 1.74 (m,2H), 2.49 (s,3H), 4.32 (t,2H), 5.83 (s,1H), 7.36 (d,1H), 7.72 (t,1H), 7.86 (d,1H). |
| 13 | sec. $C_4H_9$ | ¹H-NMR (CDCl₃, 400 MHz): 0.97 (t,3H), 134 (d,3H), 1.68 (m.2H), 2.50 (s,3H), 5.10 (m,1H), 5.83 (s,1H), 7.36 (d,1H), 7.72 (t,1H), 7.85 (d,1H). |
| 14 | $isoC_5H_{11}$ | ¹H-NMR (CDCl₃, 400 mHz): 0.95 (d,6H), 1.64 (q,2H), 1.75 (m,1H), 2.45 (s,3H), 4.35 (t,2H), 5.83 (s,1H), 7.36 (d,1H), 7.72 (t,1H), 7.85 (d,1H). |
| 15 | $nC_6H_{13}$ | ¹H-NMR (CDCl₃, 400 MHz): 0.89 (t,3H), 1.35 (m,6H), 1.75 (m,2H), 2.50 (s,3H), 4.31 (t,2H), 5.83 (s,1H), 7.36 (d,1H), 7.72 (t,1H), 7.86 (d,1H). |
| 16 | $nC_8H_{17}$ | ¹H-NMR (CDCl₃, 400 MHz): 0.88 (t,3H), 1.35 (m,10H), 1.74 (m,2H), 2.50 (s,3H), 4.31 (t,2H), 5.83 (s,1H), 7.36 (d,1H), 7.72 (t,1H), 7.86 (d,1H). |
| 17 | $isoC_4H_9$ | ¹H-NMR (CDCl₃, 400 MHz): 1.00 (d,6H), 2.07 (m,1H), 2.49 (s,3H), 4.11 (d,2H), 5.83 (s,1H), 7.37 (d,1H), 7.72 (t,1H), 7.87 (d 1H). |
| 18 | $CH_2CH=CH_2$ | ¹H-NMR (CDCl₃, 400 MHz): 2.49 (s,3H), 4.81 (m,2H), 5.30 (m,1H) 5.39 (m,1H), 5.83 (s,1H), 6.00 (m,1H), 7.38 (d,1H), 7.71 (t,1H), 7.90 (d,1H). |
| 19 | $CH_2OCH_3$ | ¹H-NMR (CDCl₃, 400 MHz): 2.50 (s,3H), 3.54 (s,3H), 5.47 (s,2H), 5.83 (s,1H), 7.39 (d,1H), 7.72 (t,1H), 7.94 (d,1H). |

EXAMPLE 20

A suspension of 2.00 g of 2-chloro-5-[3-difluoromethyl-3,6-dihydro-2,6-dioxo-4-methyl -1(2H)-pyrimidinyl]-4-fluorobenzoic acid and 2.05 g of thionyl chloride in 25 ml of benzene is heated at reflux temperature for 20 hours. The clear solution is evaporated to dryness under reduced pressure at 50° C., the residue is dissolved in 20 ml of methylene chloride and subsequently stirred at room temperature for 3.5 hours with 5 ml of propargyl alcohol and 0.55 g of pyridine. The reaction mixture is evaporated to dryness under reduced pressure, the residue is dissolved in 100 ml of ethyl acetate and the solution is extracted three times with 100 ml of water each time. The organic phase is dried over anhydrous sodium sulphate and evaporated to dryness. The resinous residue is purified by chromatography on a silica gel column using diethyl ether/n-hexane (1:1) as the eluent. There is obtained propargyl 2-chloro-5-[3-difluoromethyl-3,6-dihydro-2,6-dioxo-4-methyl -1(2H)-pyrimidinyl]-4-fluorobenzoate, ¹H-NMR (CDCl₃, 400 MHz): 7.94 ppm (d, 1H), 7.71 ppm (t, 1H), 7.39 ppm (d, 1H), 5.83 ppm (s, 1H), 4.91 ppm (d, 2H), 2.52 ppm (t, 1H), 2.50 ppm (m, 3H).

EXAMPLES 21–25

2-Chloro-5-[3-difluoromethyl-3,6-dihydro-2,6-dioxo-4-methyl-1(2H)-pyrimidinyl]-4-fluorobenzoic acid is appropriately esterified analogously to the procedure described in Example 20 in order to manufacture the compounds of formula I listed in the following Table 3.

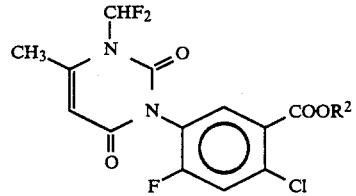

TABLE 3

| Example | R₂ | Physical data |
|---|---|---|
| 21 | $C(CH_3)_2CH=CH_2$ | ¹H-NMR (CDCl₃, 400 MHz): 1.65 (s,6H), 2.49 (s,3H), 5.15 (d,1H), 5.26 (d,1H), 5.83 (s,1H), 6.18 (m,1H), 7.34 (d,1H), 7.72 (t,1H), 7.78 (d,1H). |
| 22 | neo $C_5H_{11}$ | ¹H-NMR (CDCl₃, 400 MHz): 1.02 (s,9H), 2.50 (s,3H), 4.03 (s,2H), 5.83 (s,1H), 7.37 (d,1H), 7.72 (t,1H), 7.87 (d,1H). |
| 23 | $(CH_2)_2C(CH_3)(=CH_2)$ | ¹H-NMR (CDCl₃, 400 MHz): 1.79 (s,3H), 2.46 (m,5H), 4.43 (t,2H), 4.78 (s,1H), 4.83 (s,1H), 5.83 (s,1H), 7.36 (d,1H), 7.72 (t,1H), 7.85 (d,1H). |
| 24 | tert. $C_4H_9$ | ¹H-NMR (CDCl₃, 400 MHz): 1.58 (s,9H), 2.49 (s,3H), 5.83 (s,1H), 7.33 (d,1H), 7.72 (t,1H), |

TABLE 3-continued

| Example | R$_2$ | Physical data |
| --- | --- | --- |
| 25 | cyclopentyl | 7.76 (d,1H).<br>$^1$H-NMR (D$_6$-DMSO, 400 MHz): 1.55–1.82 (m,6H), 1.90–2.00 (m,2H), 2.44 (s,3H), 5.35 (m,1H), 6.08 (s,1H), 7.84 (d,1H), 7.90 (t,1H), 8.08 (d,1H). |

EXAMPLE 26

A 55–60% suspension of 2.9 g of sodium hydride in mineral oil is placed in 30 ml of dimethylformamide and 2 ml of toluene and the mixture is cooled to 8°–0° C. while stirring. A solution of 12 g of ethyl 3-axino-4,4,4-trifluorocarboxylate in 30 ml of dimethylformamide is added dropwise. After completion of the addition the mixture is stirred at 5° C. for 1 hour. Subsequently, the mixture is cooled to an internal temperature of −65° C. and a solution of 10 g of cyclopentyl 2-chloro-4-fluoro-5-isocyanatobenzoate in 30 ml of toluene is added dropwise thereto. The reaction mixture is stirred at 31 65° C. for a further 2.5 hours. Thereafter, 30 ml of cyclopentanol are added dropwise thereto and the reaction mixture is left to warm to room temperature. It is acidified with 10 ml of glacial acetic acid and added to 500 ml of water and the resulting aqueous solution is extracted twice with 250 ml of ethyl acetate each time. The organic phases are combined, washed in each case once with 200 ml of water and 200 ml of saturated sodium chloride solution, dried over anhydrous magnesium sulphate and evaporated under reduced pressure. The residue is purified by chromatography on a silica gel column using ethyl acetate/n-hexane (1:3) as the eluent, and there is obtained in this manner cyclopentyl 2-chloro-5-[3,6-dihydro-2,6-dioxo-4-trifluoromethyl-1(2H)-pyrimidinyl]-4-fluorobenzoate as a colourless oil. $^1$H-NMR (CDCl$_3$, 400 MHz): 1.50–2.05 (m,8H), 5.34–5.48 (m,1H). 6.23 (s,1H), 7.36 (d,1H), 7.85 (d,1H); mass spectrum (m/e): M+420(1).

EXAMPLE 27

4.5 g of cyclopentyl 2-chloro-5-[3.6-dihydro-2,6-dioxo-4-trifluoromethyl-1(2H)-pyrimidinyl]-4-fluorobenzoate, 2.1 g of potassium bicarbonate and 1.5 ml of diethyl sulphate are heated at reflux temperature in 50 ml of acetone for 4 hours. Subsequently. the solvent is distilled off and the residue is partitioned in 150 ml of diethyl ether and 150 ml of water. The aqueous phase is extracted with a further 150 ml of diethyl ether and the combined organic phases are washed twice with 150 ml of water each time, dried over anhydrous magnesium sulphate and concentrated. The residue is purified by chromatography on a silica gel column using ethyl acetate/n-hexane (1:4) as the eluent. In this manner there are obtained cyclopentyl 2-chloro-5-[3-ethyl-3,6-dihydro-2,6-dioxo-4-trifluoromethyl-1(2H)-pyrimidinyl]-4-fluorobenzoate as a colourless oil, $^1$H-NMR (CDCl$_3$, 400 MHz : 1 36 (t3H), 1.56–2.04 (m,8H), 4.02 (q,2H), 5.36–5.45 (m,1H), 6.35 (s,1H), 7.36 (d,1H), 7.82 (d,1H); mass spectrum (m/e): M+448(1), as well as cyclopentyl 2-chloro- 5-[2-ethoxy-6-oxo-4-trifluoromethyl-1(6H)-pyrimidinyl]-4-fluorobenzoate, m.p. 90°–91° C.

EXAMPLE 28

A solution of 18.0 g of isopropyl 2-chloro-5-[3-difluoromethyl-3,6-dihydro-4-methyl-2,6-dioxo-1(2H)-pyrimidinyl]-4-fluorobenzoate in 60 ml of methylene chloride is stirred intensively for 5 minutes with 100 ml of concentrated sulphuric acid and subsequently poured onto 1 kg of ice. The resulting crystals are filtered off under suction. washed twice with 50 ml of water each time and dissolved in 300 ml of methanol. The mother liquor is extracted twice with 100 ml of methylene chloride each time and the organic phase is washed with water to neutrality and combined with the methanolic solution. This solution is dried over anhydrous sodium sulphate and evaporated to dryness. The crystalline residue is stirred with 100 ml of ethyl acetate at 70° C. and cooled to room temperature, and the crystals are filtered off under suction and washed with diethyl ether. There is obtained 2-chloro-5-[3 -difluoromethyl-3.6-dihydro-4-methyl- 2,6-dioxo-1(2H)-pyrimidinyl]-4-fluorobenzoic acid, m.p. 247°–248° C.

II Production of the benzoic acids III and of their enol ethers

EXAMPLE 29

A solution of 5 g of isopropyl 2-chloro-4-fluoro-5-[2-methoxy-6-oxo-4-trifluoromethyl-1(6H) pyrimidinyl]-benzoate in 20 ml of methylene chloride is treated with 25 ml of concentrated sulphuric acid while stirring and cooling at 20°–25° C. The reaction mixture is stirred at room temperature for a further 20 minutes and poured on to 100 g of ice. The organic phase is separated, the aqueous phase is extracted twice with 15 ml of ethyl acetate each time and the combined organic phases are washed to neutrality with water. The solution is subsequently dried over anhydrous sodium sulphate and evaporated to dryness under reduced pressure. The resinous residue is recrystallized from diethyl ether/n-hexane. There is obtained 2-chloro-4-fluoro-5-[2 -methoxy-6-oxo-4-trifluoromethyl-1(6H)-pyrimidinyl]-benzoic acid, m.p. 205°–210° C.

In an analogous manner.

using isopropyl 2-chloro-4-fluoro-5-[2-methoxy-6-oxo-4-pentafluoroethyl-1(6H)-pyrimidinyl]-benzoate there is obtained 2-chloro-4-fluoro-5-[2-methoxy-6-oxo-4-pentafluoroethyl-1(6H)-pyrimidinyl]-benzoic acid, m.p. 197°–199° C.;

using isopropyl 2-chloro-4-fluoro-5-[5-fluoro-2-methoxy-6-oxo-4-trifluoromethyl-1(6H)-pyrimidinyl]-benzoate there is obtained 2-chloro-4-fluoro-5-[5-fluoro-2-methoxy- 6-oxo-4-trifluoromethyl-1(6H)-pyrimidinyl]-benzoic acid, m.p. 199°–201° C.;

using isopropyl 2-chloro-4-fluoro-5-[3,6 -dihydro-2,6-dioxo-3-methyl-4-trifluoromethyl-1(2H)-pyrimidinyl]-benzoate there is obtained 2-chloro-5-[3,6-dihydro-2,6-dioxo-3-methyl-4-trifluoromethyl-1(2H)-pyrimidinyl]-4-fluorobenzoate. m.p. 239°–242° C.;

using isopropyl 2-chloro-5-[3.6-dihydro-2,6-dioxo-3-methyl-4 trifluoromethyl-1(2H)-pyrimidinyl]-benzoate there is obtained 2chloro-5-[3,6-dihydro-2,6-dioxo-3-methyl-4-trifluoromethyl-1(2H)-pyrimidinyl]-benzoic acid, m.p. 235°–236° C.;

using isopopyl 2-chloro-5-[3,6-dihydro-2,6-dioxo-3-methyl-4-pentafluoroethyl-1(2H)-pyrimidinyl]-4-fluorobenzoate there is obtained 2-chloro-5-[3,6-dihydro-2,6-dioxo-3-methyl-4-pentafluoroethyl-1(2H)-pyrimidinyl]-4-fluorobenzoic acid, m.p. 229°–231° C.;

using isopropyl 2-chloro-5-[3,6-dihydro-3,4-dimethyl-2,6-dioxo-1(2H)-pyrimidinyl]-4-fluorobenzoate there is obtained 2-chloro-5-[3,6-dihydro-3,4-dimethyl-2,6-dioxo-1(2H)-pyrimidinyl]-4-fluorobenzoic acid, m.p. 236°-239° C.;

using isopropyl 2-chloro-5-[2-methoxy-6-oxo-4-trifluoromethyl-1(6H)-pyrimidinyl]-benzoate there is obtained 2-chloro-5-[2-methoxy-6-oxo-4 trifluoromethyl-1(6H)-pyrimidinyl]-benzoic acid, m.p. 265°-268° C.

III. Production of the 3-Isocyanatobenzoic acid esters of formula XI:

EXAMPLE 30

The cyclopentyl 2-chloro-4-fluoro-5-isocyanatobenzoate required as the starting material in Example 26 can be 26 can be produced as follows:

A mixture of 100 g of 2-chloro-4-fluoro-5-nitrobenzoic acid, 50 ml of thionyl chloride and 100 ml of benzene is heated at reflux temperature for 4 hours with the addition of 0.5 ml of dimethylformamide. Subsequently, the solvent is distilled off; crude 2-chloro-4-fluoro-5-nitrobenzoyl chloride remains behind.

The 2-chloro-4-fluoro-5-nitrobenzoyl chloride is dissolved in 400 ml of dioxan and the solution is added dropwise at room temperature while stirring to a solution of 36 ml of cyclopentanol and 42 ml of pyridine in 300 ml of dioxan. After completion of the addition the mixture is stirred at room temperature for a further 4 hours, added to 300 g of ice and 300 ml of 2N hydrochloric acid and extracted twice with 300 ml of ethyl acetate each time.

The combined organic phases are washed once with 300 ml of 2N hydrochloric acid and three times with 150 ml of saturated sodium chloride solution each time, dried over anhydrous magnesium sulphate and concentrated. After recrystallization from diisopropyl ether/n-hexane there is obtained cyclopentyl 2-chloro-4-fluoro-5-nitrobenzoate, m.p. 44°-45° C.

71 g of iron powder are placed in 190 ml of ethanol, 50 ml of water and 5 ml of 32% hydrochloric acid while stirring and the whole is heated to 75° C. (internal temperature). A warm solution of 100 g of cyclopentyl 2-chloro-4-fluoro-5-nitrobenzoate in 50 ml of ethanol is added dropwise to this mixture. The reaction mixture is stirred at 70°-75° C. (internal temperature) for a further 2 hours, cooled, after cooling suction filtered over Celite and the residue on the suction filter is rinsed with 500 ml of water followed by 200 ml of ethyl acetate. The filtrate is brought to a PH value of 8 with saturated potassium bicarbonate solution and the resulting brown precipitate is filtered off over Celite. The filtrate is extracted twice with 400 ml of ethyl acetate each time. the combined organic phases are washed twice with 200 ml of saturated sodium chloride solution each time, dried over anhydrous magnesium sulphate and concentrated. Then, the residue is purified by chromatography on a silica gel column using ethyl acetate/n-hexane (1:4) as the eluent and crystallized from diisopropyl ether/n-hexane. In this manner there is obtained cyclopentyl 5-amino-2-chloro-4-fluorobenzoate, m.p. 61°-62° C.

A solution of 19 g of cyclopentyl 5-amino 2chloro-4-fluorobenzoate in 100 ml of ethyl acetate is added dropwise while stirring to a solution, warmed to 70° (internal temperature), of 9 ml of diphosgene in 40 ml of ethyl acetate. The reaction mixture is then heated at reflux temperature for 2 hours. Subsequently, the solvent is distilled off and the residue is distilled in a bulb tube under greatly reduced pressure. There is then obtained cyclopentyl 2-chloro-4-fluoro-5-isocyanato-benzoate, b.p. 160° C./0.06 mm Hg, which is required as the starting material in Example 26.

IV. Formulation Examples

EXAMPLE 31

An emulsifiable concentrate contains the following ingredients:

| | |
|---|---|
| Compound in accordance with the invention (active substance) | 50 g/l |
| N-Methylpyrrolidone (auxiliary solvent) | 200 g/l |
| Nonylphenol-(10)ethoxylate (non-ionic emulsifier) | 50 g/l |
| Calcium dodecylbenzenesulphonate (anionic emulsifier) | 25 g/l |
| Mixture of alkylbenzenes (solvent) ad | 1000 ml |

The active substance and the emulsifiers are dissolved in the auxiliary solvent while stirring and the solution is made up to 1 liter with the solvent.

The resulting emulsifiable concentrate can be emulsified in water and then gives a ready-for-use spray liquor having the desired concentration.

EXAMPLE 32

The ingredients listed hereinafter are mixed with one another for the manufacture of a 25% spray liquor:

| | |
|---|---|
| Compound in accordance with the invention (active substance) | 25 g |
| Silicic acid, hydrated (carrier material, grinding agent) | 5–25 g |
| Sodium lauryl sulphate (wetting agent) | 1 g |
| Sodium lignosulphonate (dispersing agent) | 2 g |
| Kaolin (carrier material) | 67–47 g |
| | 100 g |

The mixture is subsequently finely ground using a pinned disc mill or comparable milling apparatus.

Upon stirring in water the resulting spray powder gives a fine suspension which is suitable as a ready-for-use spray liquor.

We claim:

1. Compounds of the formula

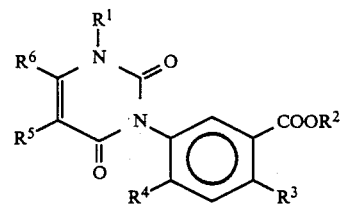

I wherein
R$^1$ signifies hydrogen, C$_{1-4}$-alkyl, C$_{3\text{ or }4}$-alkenyl, C$_{3\text{ or }4}$-alkynyl or C$_{1-4}$-haloalkyl,
R$^2$ signifies a group

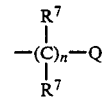

or, where $R^1$ signifies haloalkyl, also hydrogen $C_{1-8}$-alkyl, $C_{2-8}$-alkenyl, $C_{2-8}$-alkynyl or $C_{2-8}$-alkoxyalkyl, $R^3$ signifies halogen or cyano, $R^4$ signifies hydrogen or halogen, $R^5$ signifies hydrogen, fluorine or $C_{1-4}$-alkyl, $R^6$ signifies $C_{1-4}$-alkyl or $C_{1-4}$-haloalkyl, the symbols $R^7$ each independently signify hydrogen or $C_{1-3}$-alkyl and n signifies 0, 1 or 2, and Q signifies a saturated three- to seven-membered carbocyclic or heterocyclic residue which is optionally substituted with one or more $C_{1-4}$-alkyl residues, whereby the heterocyclic residue has 1 or 2 hetero atoms selected from oxygen and sulphur and optionally a keto function in the ring, Q signifies a phenyl residue which is optionally mono- or multiply-substituted with halogen, $C_{1-4}$-alkyl, $C_{1-4}$-haloalkyl, $C_{1-4}$-alkoxy, $C_{1-4}$-alkylthio, nitro and/or cyano and which additionally can bear a fused, saturated, carbocyclic or heterocyclic five- to seven-membered ring, whereby the heterocycle has 1 or 2 oxygen atoms in the ring, and the corresponding enol ethers of those compounds of formula I in which $R^1$ is different from hydrogen or $C_{1-4}$-haloalkyl as well as alkali metal, alkaline earth metal, ammonium or organic base salts of those compounds of formula I in which $R^1$ or $R^2$ signifies hydrogen.

2. Compounds according to claim 1, wherein $R^1$ signifies hydrogen, $C_{1-4}$-alkyl, $C_{3 \text{ or } 4}$-alkenyl or $C_{3 \text{ or } 4}$-alkynyl, and their enol ethers and salts.

3. Compounds according to claim 1, wherein $R^1$ signifies $C_{1-4}$-haloalkyl, $R^2$ signifies hydrogen, $C_{1-8}$-alkyl, $C_{2-8}$-alkenyl, $C_{2-8}$-alkynyl, $C_{2-8}$-alkoxyalkyl or a group -$(CR\ R)_n$-Q and Q signifies either a saturated 3- to 7-membered carbocyclic or heterocyclic residue which is optionally substituted with one or more $C_{1-4}$-alkyl residues, whereby the heterocyclic residue has 1 or 2 heteroatoms selected from oxygen or sulphur in the ring, or signifies a phenyl residue which is optionally mono- or multiply-substituted with halogen, $C_{1-4}$-alkyl, $C_{1-4}$-haloalkyl, $C_{1-4}$-alkoxy, $C_{1-4}$-alkylthio, nitro and/or cyano, and the salts of these compounds.

4. Compounds according to claim 2, wherein $R^1$ signifies methyl.

5. Compounds according to claim 3, wherein $R^1$ signifies difluoromethyl.

6. Compounds according to any one of claims 1 to 3, wherein $R^3$ signifies chlorine or bromine and $R^4$ signifies fluorine.

7. Compounds according to any one of claims 1 to 3, wherein $R^3$ signifies chlorine or bromine and $R^4$ wherein R signifies hydrogen.

8. Compounds according to any one of claims 1 to 3, wherein $R^5$ signifies hydrogen. fluorine or methyl.

9. Compounds according to any one of claims 1 to 3, wherein $R^6$ signifies $C_{1-4}$-alkyl.

10. Compounds according to any one of claims 1 to 3, wherein $R^2$ signifies a group -$(CR^7R^7)_n$-Q in which each $R^7$ signifies hydrogen and n signifies 0 or 1.

11. A compound according to claim 2, selected from cycloheptyl 2-chloro-5-[3,6-dihydro-2,6-dioxo-3-methyl-4-trifluoromethyl-1(2H)-pyrimidinyl]-4-fluorobenzoate, 3-tetrahydrofuryl 2-chloro-5-[3,6-dihydro-2,6-dioxo-3-methyl-4-trifluoromerhyl-1(2H)-pyrimidinyl]-4-fluorobenzoate, 1,3-dioxan-5-yl 2-chloro-5-[3,6-dihydro-2,6-dioxo-3-methyl-4-trifluoromethyl-1(2H)-pyrimidinyl]-4-fluorobenzoate, cyclopropylmethyl 2-chloro-5-[3,6-dihydro-2,6-dioxo-3-methyl-4-trifluoromethyl-1(2H)-pyrimidinyl]-4-fluorobenzoate, tetrahydrofurfuryl 2-chloro-5-[3,6-dihydro-2,6-dioxo-3-methyl-4-trifluoromethyl-1(2H)-pyrimidinyl]-4-fluorobenzoate, 1,3-dioxolan-4-ylmethyl 2-chloro-5-[3,6-dihydro-2,6-dioxo-3-methyl-4-trifluoromethyl-1(2H)-pyrimidinyl]-4-fluorobenzoate, benzyl 2-chloro-5-[3,6-dihydro-2,6-dioxo-3-methyl-4-trifluoromethyl-1(2H)-pyrimidinyl]-4-fluorobenzoate, 4,4-dimethyl-2-oxo-tetrahydrofuran-3-yl 2-chloro-5-[3,6-dihydro-2,6-dioxo-3-methyl-4-trifluoromethyl-1(2H)-pyrimidinyl]-4-fluorobenzoate, cyclopentyl 2-chloro-5-[3,6-dihydro-2,6-dioxo-3-methyl-4-trifluoromethyl-1(2H)-pyrimidinyl]-4-fluorobenzoate, 1-cyclopropylethyl 2-chloro-5-[3,6-dihydro-2,6-dioxo-3-methyl-4-trifluoromethyl-1(2H)-pyrimidinyl]-4-fluorobenzoate and cyclohexyl 2-chloro-5-[3,6-dihydro-2,6-dioxo-3-methyl-4-trifluoromethyl-1(2H)-pyrimidinyl]-4-fluorobenzoate.

12. A compound according to claim 3, selected from isopropyl 2-chloro-5-[3-difluoromethyl-3,6-dihydro-4-methyl-2,6-dioxo-1(2H)-pyrimidinyl]-4-fluorobenzoate, 2-chloro-5-[3-difluoromethyl-3,6-dihydro-4-methyl-2,6-dioxo-1(2H)-pyrimidinyl]-4-fluorobenzoic acid, isopropyl 5-[4-ethyl-3-difluormethyl-3,6-dihydro-2,6-dioxo-1(2H)-pyrimidinyl]-2-chloro-4-fluorobenzoate, isopropyl 5-[4-ethyl-3-difluoromethyl-3,6-dihydro-2,6-dioxo-1(2H)-pyrimidinyl]-2-bromo-4-fluorobenzoate, isopropyl 2-bromo-5-[3-difluoromethyl-3,6-dihydro-4-methyl-2,6-dioxo-1(2H)-pyrimidinyl]-4-fluorobenzoate, 2-propynyl 2-chloro-5-[3-difluoromethyl-3,6-dihydro-4-methyl-2,6-dioxo-1(2H)-pyrimidinyl]-4-fluorobenzoate and methyl 2-chloro-5-[3-difluoromethyl-3,6-dihydro-4-methyl-2,6-dioxo-1(2H)-pyrimidinyl]-4-fluorobenzoate.

13. A compound according to claim 1, selected from cyclopropylmethyl 2-chloro-5-[3,6-dihydro-3,4-dimethyl-2,6-dioxo-1(2H)-pyrimidinyl]-4-fluorobenzoate, 1-cyclopropylethyl 2-chloro-5-[3,6-dihydro-3,4-dimethyl-2,6-dioxo-1(2H)-pyrimidinyl]4-fluorobenzoate, cyclopentyl 2-chloro-5-[3,6-dihydro 3,4-dimethyl-2,6-dioxo-1(2H)-pyrimidinyl]-4-fluorobenzoate, cyclohexyl 2-chloro-5-[3,6-dihydro-3,4-dimethyl-2,6-dioxo-1(2H)-pyrimidinyl]-4-fluorobenzoate, cycloheptyl 2-chloro-5-[3,6-dihydro-3,4-dimethyl-2,6-dioxo- 1(2H)-pyrimidinyl]-4-fluorobenzoate, 3-tetrahydrofuryl 2-chloro-5-[3,6-dihydro-3,4-dimethyl-2,6-dioxo-1(2H)-pyrimidinyl]4-fluorobenzoate, 1,3-dioxan-5-yl 2-chloro-5-[3,6 dihydro-3,4-dimethyl-2,6-dioxo-1(2H)-pyrimidinyl-]-4-fluorobenzoate, (1,3 dioxolan-4-yl)methyl 2-chloro-5 [3,6-dihydro-3,4-dimethyl-2,6-dioxo-1(2H)-pyrimidinyl]-4-fluorobenzoate, benzyl 2-chloro 5-[3,6-dihydro-3,4-dimethyl-2,6-dioxo-1(2H)-pyrimidinyl]-4-fluorobenzoate and tetrahydrofurfuryl 2-chloro-5-[3,6-dihydro-3,4-dimethyl-2,6-dioxo-1(2H)-pyrimidinyl]-4-fluorobenzoate.

14. Compounds of the formula:

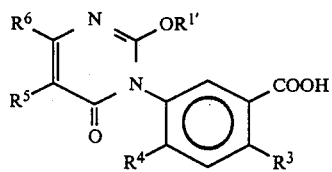

wherein
R$^{1'}$ signifies C$_{1-4}$-alkyl, C$_{3 \text{ or } 4}$-alkenyl or C$_{3 \text{ or } 4}$-alkynyl,
R$^3$ signifies halogen or cyano,
R$^4$ signifies hydrogen or halogen,
R$^5$ signifies hydrogen, fluorine or C$_{1-4}$-alkyl and
R$^6$ signifies C$_{1-4}$-alkyl or C$_{1-4}$-haloalkyl,
as well as the alkali metal, alkaline earth metal, ammonium or organic base salts thereof.

15. A weed control composition, characterized in that it contains an effective amount of at least one compound of the formula

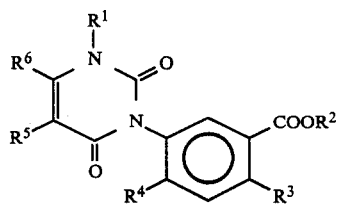

wherein
R$^1$ signifies hydrogen, C$_{1-4}$-alkyl, C$_{3 \text{ or } 4}$-alkenyl, C$_{3 \text{ or } 4}$-alkynyl or C$_{1-4}$-haloalkyl,
R$^2$ signifies a group

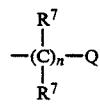

or, where R$^1$ signifies haloalkyl, also hydrogen, C$_{1-8}$-alkyl, C$_{2-8}$-alkenyl, C$_{2-8}$-alkynyl or C$_{2-8}$-alkoxyalkyl,
R$^3$ signifies halogen or cyano,
R$^4$ signifies hydrogen or halogen,
R$^5$ signifies hydrogen, fluorine or C$_{1-4}$-alkyl,
R$^6$ signifies C$_{1-4}$-alkyl or C$_{1-4}$-haloalkyl,
the symbols R$^7$ each independently signify hydrogen or C$_{1-3}$-alkyl and
n signifies 0, 1 or 2, and
Q signifies a saturated three- to seven-membered carbocyclic or heterocyclic residue which is optionally substituted with one or more C$_{1-4}$-alkyl residues, whereby the heterocyclic residue has 1 or 2 hetero atoms selected from oxygen and sulphur and optionally a keto function in the ring, or
Q signifies a phenyl residue which is optionally mono- or multiply-substituted with halogen, C$_{1-4}$-alkyl, C$_{1-4}$-haloalkyl, C$_{1-4}$-alkoxy, C$_{1-4}$-alkylthio, nitro and/or cyano and which additionally can bear a fused, saturated, carbocyclic or heterocyclic five- to seven-membered ring, whereby the heterocycle has 1 or 2 oxygen atoms in the ring,
or of an enol ether of such a compound I in which R$^1$ is different from hydrogen or C$_{1-4}$-haloalkyl or of an alkali metal, alkaline earth metal, ammonium or organic base salt of such a compound I in which R$^1$ or R$^2$ is hydrogen, as well as formulation adjuvants.

16. A weed control composition according to claim 15, characterized in that it contains an effective amount of at least one compound selected from the group
cycloheptyl 2-chloro-5-[3,6-dihydro-2,6-dioxo-3-methyl-4-trifluoromethyl-1(2H)-pyrimidinyl]-4fluorobenzoate,
3-tetrahydrofuryl 2-chloro-5-[3,6-dihydro-2,6-dioxo-3-methyl-4-trifluoromethyl-1(2H)-pyrimidinyl]-4-fluorobenzoate,
1,3-dioxan-5-yl 2-chloro-5-[3,6-dihydro-2,6-dioxo-3-methyl-4-trifluoromethyl-1(2H)-pyrimidinyl]-4-fluorobenzoate,
cyclopropylmethyl 2-chloro-5-[3,6-dihydro-2,6-dioxo-3-methyl 4 trifluoromethyl-1(2H)-pyrimidinyl]-4-fluorobenzoate,
tetrahydrofurfuryl 2-chloro-5-[3,6-dihydro-2,6-dioxo-3-methyl-4-trifluoromethyl 1(2H)-pyrimidinyl]-4-fluorobenzoate,
1,3-dioxolan-4-ylmethyl 2-chloro-5-[3,6-dihydro-2,6-dioxo-3-methyl-4-trifluoromethyl-1(2H)-pyrimidinyl]-4-fluorobenzoate,
benzyl 2-chloro-5-[3,6-dihydro-2,6-dioxo-3-methyl-4-trifluoromethyl-1(2H)-pyrimidinyl]-4-fluorobenzoate,
4,4-dimethyl-2-oxo-tetrahydrofuran-3-yl 2-chloro-5-[3,6-dihydro-2,6 dioxo-3-methyl-4-trifluoromethyl-1(2H)-pyrimidinyl]-4-fluorobenzoate,
cyclopentyl 2-chloro-5-[3,6-dihydro-2,6-dioxo-3-methyl-4-trifluoromethyl-1(2H)-pyrimidinyl]-4-fluorobenzoate,
1-cyclopropylethyl 2-chloro-5-[3,6-dihydro-2,6-dioxo-3-methyl-4-trifluoromethyl-1(2H)-pyrimidinyl]-4-fluorobenzoate and
cyclohexyl 2-chloro-5-[3,6-dihydro-2,6-dioxo-3-methyl-4-trifluoromethyl-1(2H)-pyrimidinyl]-4-fluorobenzoate
as well as formulation adjuvants.

17. A weed control composition according to claim 15, characterized in that it contains an effective amount of at least one compound selected from the group
isopropyl 2-chloro-5-[3-difluoromethyl-3,6-dihydro-4-methyl-2,6-dioxo-1(2H)-pyrimidinyl]-4-fluorobenzoate,
2-chloro-5-[3-difluoromethyl-3,6-dihydro-4-methyl-2,6-dioxo-1(2H)-pyrimidinyl]-4-fluorobenzoic acid,
isopropyl 5-[4-ethyl-3-difluormethyl-3,6-dihydro-2,6-dioxo-1(2H)-pyrimidinyl]-2-chloro-4-fluorobenzoate,
isopropyl 5-[4-ethyl-3-difluoromethyl-3,6-dihydro-2,6-dioxo-1(2H)-pyrimidinyl]-2-bromo-4-fluorobenzoate,
isopropyl 2-bromo-5-[3-difluoromethyl-3,6-dihydro-4-methyl-2,6-dioxo-1(2H)-pyrimidinyl]-4-fluorobenzoate,
2-propynyl 2-chloro-5-[3-difluoromethyl-3,6-dihydro-4-methyl-2,6-dioxo-1(2H)-pyrimidinyl]-4-fluorobenzoate and methyl 2-chloro-5-[3-difluoromethyl-3,6-dihydro-4-methyl 2,6-dioxo-1(2H)-pyrimidinyl]-4-fluorobenzoate
as well as formulation adjuvants.

18. A weed control composition according to claim 15, characterized in that it contains an effective amount of at least one compound selected from the group
cyclopropylmethyl 2-chloro-5-[3,6-dihydro-3,4-dimethyl-2,6-dioxo-1(2H)-pyrimidinyl]-4-fluorobenzoate,
1-cyclopropylethyl 2-chloro-5-[3,6-dihydro-3,4-dimethyl-2,6-dioxo-1(2H)-pyrimidinyl]-4-fluorobenzoate, cyclopentyl 2-chloro-5-[3,6-dihydro-3,4-dimethyl-2,6-dioxo-1(2H)-pyrimidinyl]-4-fluorobenzoate, cyclohexyl 2-chloro-5-[3,6-dihydro-3,4-dimethyl-2,6-dioxo-1(2H)-pyrimidinyl]-4-fluorobenzoate, cycloheptyl 2-chloro-5-[3,6-dihydro-3,4-dimethyl-2,6-dioxo-1(2H)-pyrimidinyl]-4-fluorobenzoate, 3-tetrahydrofuryl 2-chloro-5-[3,6-dihydro-3,4-dimethyl-2,6-dioxo-1(2H)-pyrimidinyl]-4-fluorobenzoate, 1,3-dioxan-5-yl 2-chloro-5-[3,6-dihydro-3,4-dimethyl-2,6-dioxo-1(2H)-pyrimidinyl]-4-fluorobenzoate, (1,3-dioxolan-4-yl)methyl 2-chloro-5-[3,6-dihydro-3,4-dimethyl-2,6-dioxo-1(2H)-pyrimidinyl]-4-fluorobenzoate, benzyl 2-chloro-5-[3,6-dihydro 3,4-dimethyl-2,6-dioxo-1(2H)-pyrimidinyl]-4-fluorobenzoate and tetrahydrofurfuryl 2 chloro-5-[3,6-dihydro-3,4-dimethyl-2,6-dioxo-1(2H)-pyrimidinyl]-4-fluorobenzoate as well as formulation adjuvants.

19. A weed control composition, characterized in that it contains an effective amount of at least one compound of the formula

IIIa wherein $R^{1'}$ signifies $C_{1-4}$-alkyl, $C_{3 \text{ or } 4}$-alkenyl or $C_{3 \text{ or } 4}$-alkynyl, $R^3$ signifies halogen or cyano, $R^4$ signifies hydrogen or halogen, $R^5$ signifies hydrogen, fluorine or $C_{1-4}$-alkyl and $R^6$ signifies $C_{1-4}$-alkyl or $C_{1-4}$-haloalkyl, or of an alkali metal, alkaline earth metal, ammonium or organic base salt thereof, as well as formulation adjuvants.

* * * * *